(12) United States Patent
Pevarello et al.

(10) Patent No.: US 6,387,900 B1
(45) Date of Patent: May 14, 2002

(54) 3(5)-UREIDO-PYRAZOLE DERIVATIVES PROCESS FOR THEIR PREPARATION AND THEIR USE AS ANTITUMOR AGENTS

(75) Inventors: Paolo Pevarello, Pavia; Paolo Orsini, Varese; Gabriella Traquandi; Mario Varasi, both of Milan, all of (IT); Edward L. Fritzen; Martha A. Warpehoski, both of Portage, MI (US); Betsy S. Pierce, Kalamazoo, MI (US)

(73) Assignees: Pharmacia & Upjohn S.p.A., Milan (IT); Pharmacia & Upjohn Co., Kalamazoo, MI (US)

( * ) Notice: Subject to any disclaimer, the term of this patent is extended or adjusted under 35 U.S.C. 154(b) by 0 days.

(21) Appl. No.: 09/372,833

(22) Filed: Aug. 12, 1999

(51) Int. Cl.$^7$ .................... C07D 231/40; C07D 403/12; A61K 31/415; A61K 31/496
(52) U.S. Cl. ................ 514/236.5; 548/364.1; 548/371.4; 514/407; 514/254.05; 544/140; 544/371
(58) Field of Search ............ 548/364.1, 371.4; 514/407, 236.5, 254.05; 544/140, 371

(56) References Cited

U.S. PATENT DOCUMENTS 6,043,246 A   3/2000   Fukami et al.

FOREIGN PATENT DOCUMENTS

| WO | WO 96/14843 | | 5/1996 |
|---|---|---|---|
| WO | WO 98/24768 | * | 6/1998 |
| WO | WO 98/52941 | | 11/1998 |
| WO | WO 99/32111 | | 7/1999 |

OTHER PUBLICATIONS

Tomoko Hosoi et al., "Evidence for CDK5 as a Major Activity Phosphorylating Tau Protein in Porcine Brain Extract", J. Biochem. vol. 117, pp. 741–749, 1995.
Kevin R. Webster, "The Therapeutic Potential of Targeting the Cell Cycle", Ashley Publications Ltd., Exp. Opin. Invest. Drugs, vol. 7, No. 6, pp. 865–887, 1998.
Chemical Abstracts of Japan, Raymond S. Brinkmeyer et al., "Dimerization of Pyrazolyl-5-hydroxypyrrolidinones to Tetrazocines", Accession No. 1990:216898, 1990.

* cited by examiner

Primary Examiner—Richard L. Raymond
Assistant Examiner—Hong Liu
(74) Attorney, Agent, or Firm—Oblon, Spivak, McClelland, Maier & Neustadt, P.C.

(57) ABSTRACT

3-ureido-pyrazole derivatives represented by formula (I):

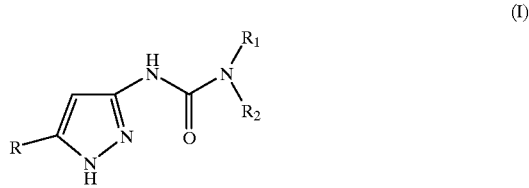

where R, $R_1$ and $R_2$ are as described herein, or pharmnaceutically acceptable salts thereof; are useful, for example, for the treatment of cancer, cell proliferative disorders, Alzheimer's disease, viral infections, auto-immune diseases or neurodegenerative diseases.

28 Claims, No Drawings

3(5)-UREIDO-PYRAZOLE DERIVATIVES PROCESS FOR THEIR PREPARATION AND THEIR USE AS ANTITUMOR AGENTS

BACKGROUND OF THE INVENTION

1. Field of the Invention

The present invention relates to 3(5)-ureido-pyrazole derivatives, to a process for their preparation, to pharmaceutical compositions containing them and to their use as therapeutic agents, particularly in the treatment of cancer and proliferative disorders.

2. Discussion of the Background

Several cytotoxic drugs such as, e.g. fluorouracil (5-FU), doxorubicin and camptothecins, cause damage to DNA or to affect cellular metabolic pathways and thus cause, in many cases, an indirect block of the cell cycle. Therefore, by producing an irreversible damage to both normal and tumor cells, these agents result in a significant toxicity and side-effects.

In this respect, compounds capable of being highly specific antitumor agents by selectively leading to tumor cell arrest and apoptosis, with comparable efficacy but reduced toxicity than the currently available drugs, are desirable.

It is well known that progression through the cell cycle is governed by a series of checkpoint controls, otherwise referred to as restriction points, which are regulated by a family of enzymes known as the cyclin-dependent kinases (cdk). In turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of metaphases.

For a general reference to cyclins and cyclin-dependent kinases see, for instance, Kevin R. Webster et al. in Exp. Opin. Invest. Drugs, 1998, Vol. 7(6), 865–887.

Checkpoint controls are defective in tumor cells due, in part, to disregulation of cdk activity. For example, altered expression of cyclin E and cdk's has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

SUMMARY OF THE INVENTION

It is an object of the invention to provide compounds which are useful in treating cell proliferative disorders associated with an altered cell dependent kinase activity. It is another object to provide compounds which have cdk/cyclin kinase inhibitory activity. It is another object of the invention to provide compounds which are useful in therapy as antitumor agents but lack, in terms of both toxicity and side effects, the drawbacks associated with currently available antitumor drugs as discussed above.

The present inventors have now discovered that 3-ureido-pyrazoles have cdk/cyclin kinase inhibitory activity and are thus useful in therapy as antitumor agents and lack, in terms of both toxicity and side effects, the aforementioned drawbacks of known antitumor drugs.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation, these 3-ureido-pyrazole derivatives are also useful in the treatment of a variety of cell proliferative disorders such as, for instance, benign prostate hyperplasia, familial adenomatosis polyposis, neurofibromatosis, psoriasis, vascular smooth cell proliferation associated with atherosclerosis, pulmonary fibrosis, arthritis glomerulonephritis and post-surgical stenosis and restenosis.

The compounds of the invention may be useful in the treatment of Alzheimer's disease, as suggested by the fact that cdk5 is involved in the phosphorylation of tau protein (J. Biochem., 117, 741–749, 1995).

The compounds of this invention, as modulators of apoptosis, may also useful in the treatment of cancer, viral infections, prevention of AIDS development in HIV-infected individuals, autoimmune diseases and neurodegenerative disorders.

The compounds of this invention may also be useful in inhibiting tumor angiogenesis and metastasis.

The compounds of this invention may also act as inhibitors of other protein kineses, e.g. protein kinase C, her2, raf1, MEK1, MAP kinase, EGF receptor, PDGF receptor, IGF receptor, PI3 kinase, wee1 kinase, Src, Ab1 and thus be effective in the treatment of diseases associated with other protein kineses.

Accordingly, the present invention provides a method for the treatment of cell proliferative disorders associated with an altered cell dependent kinase activity, comprising administering to a mammal in need thereof an effective amount of a compound represented by formula (I):

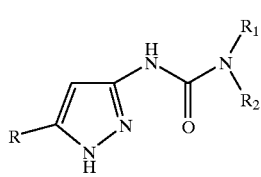

(I)

where
R is a $C_3$–$C_6$ cycloalkyl group optionally substituted with a straight or branched $C_1$–$C_6$ alkyl group or is a $C_1$–$C_6$ alkyl or arylalkyl group, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

$R_1$ is —CH$_2$)$_n$—$R_3$;

n is 0 or an integer from 1 to 4;

$R_3$ is hydrogen, hydroxy, amino, or a group selected from the group consisting of cycloalkyl, aryl and heterocyclyl, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

$R_2$ is hydrogen, or $R_2$ and $R_1$, together with the nitrogen atom to which they are bonded, form a heterocyclyl or heteroaryl group, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

or pharmaceutically acceptable salts thereof;

provided that when n is 0 and $R_2$ is hydrogen, R is a $C_3$–$C_6$ cycloalkyl group optionally substituted with a straight or branched $C_1$–$C_6$ alkyl group.

According to a preferred embodiment of the invention, the cell proliferative disorder is selected from the group consisting of cancer, Alzheimer's disease, viral infections, auto-immune diseases and neurodegenerative disorders.

Examples of types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

According to another preferred embodiment of the invention, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis, and post-surgical stenosis and restenosis.

In addition, the inventive method provides tumor angiogenesis and metastasis inhibition. The inventive method may also provide cell cycle inhibition or cdk/cyclin dependent inhibition.

The present invention also provides a 3-ureido-pyrazole derivative represented by formula (I):

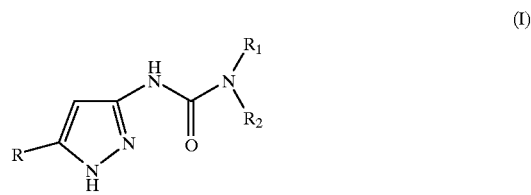

(I)

where

R is a $C_1$–$C_6$ alkyl, aryl or arylalkyl group, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

$R_1$ is —CH$_2$)$_n$—$R_3$;

n is 0 or an integer from 1 to 4;

$R_3$ is hydrogen, hydroxy, amino, or a group selected from the group consisting of cycloalkyl, aryl and heterocyclyl, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

$R_2$ is hydrogen, or $R_2$ and $R_1$, together with the nitrogen atom to which they are bonded, form a heterocyclyl or heteroaryl group, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

or a pharmaceutically acceptable salt thereof;

provided that when n is 0 and $R_2$ is hydrogen, R is a $C_3$–$C_6$ cycloalkyl group optionally substituted with a straight or branched $C_1$–$C_6$ alkyl group.

The present invention also provides a process for preparing the 3-ureido-pyrazole derivative, or a pharmaceutically acceptable salt thereof, by:

(a) reacting a compound represented by formula (II):

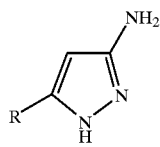

(II)

with a compound represented by formula (III):

$R_1$—NCO (III)

where R and $R_1$ are as defined above, to produce a compound represented by formula (IV):

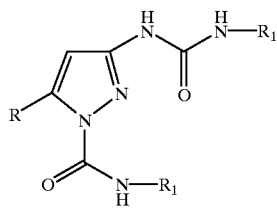

(IV)

where R and $R_1$ are as defined above; and (b) selectively hydrolizing a compound represented by formula (IV) in a basic medium to produce the 3-ureido-pyrazole derivative represented by formula (I).

The present invention also provides a process for preparing the 3-ureido-pyrazole derivative, or a pharmaceutically acceptable salt thereof, by:

(c) reacting a compound represented by formula (V):

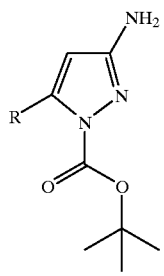

(V)

wherein R is defined above, with 4-nitrophenyl chloroformate, or a polymer supported form of 4-nitrophenyl chloroformate, to produce a compound represented by formula (VI), or a polymer supported form of the compound represented by formula (VI):

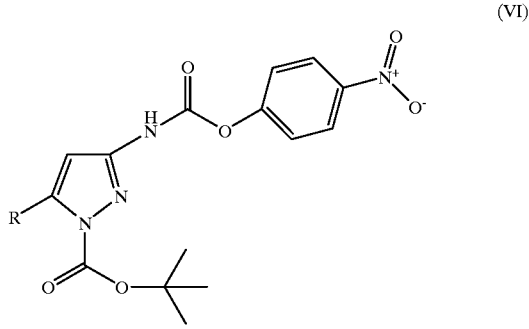

(VI)

where R is defined above;

(d) reacting a compound represented by formula (VI) with a compound represented by formula (VII):

$R_1R_2NH$ (VII)

where $R_1$ and $R_2$ are as defined above, to produce a compound represented by formula (VIII):

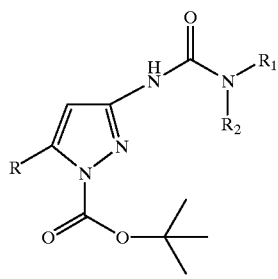

(VIII)

where R, $R_1$ and $R_2$ are as defined above;

(e) hydrolyzing a compound represented by formula (VIII) in an acidic medium to produce the 3-ureido-pyrazole derivative represented by formula (I); and, optionally, converting the 3-ureido-pyrazole derivative represented by formula (I) into another 3-ureido-pyrazole derivative represented by formula (I), and/or into a salt thereof.

The present invention also provides a pharmaceutical composition, comprising the 3-ureido-pyrazole derivative and at least one pharmaceutically acceptable carrier and/or diluent.

A more complete appreciation of the invention and many of the attendant advantages thereof will be readily obtained as the same becomes better understood by reference to the following detailed description.

DETAILED DESCRIPTION OF THE INVENTION

Several 3-ureido-pyrazole derivatives are known in the art as pesticides, herbicides or even as therapeutic agents. Among them are, as an example, heteroaryl-pyrazoles active as p38 kinase inhibitors (WO 9852941, G. D. Searle and Co.). Aryl-ureido-pyrazoles such as, for instance, phenyl-ureidopyrazoles are also known in the art as p38 kinase inhibitors (WO 99/32111, Bayer Co.). Several 5-aryl-(1H- pyrazol-5-yl)-urea derivatives are known in the art as neuropeptide Y antagonists useful as hypolipemic agents (WO 98//24768, Banyu pharmaceutical Co.).

As will be readily apparent to one skilled in the art, the unsubstituted ring nitrogen pyrazoles, as in the compounds of the present invention, are known to rapidly equilibrate, in solution, as admixtures of both tautomers:

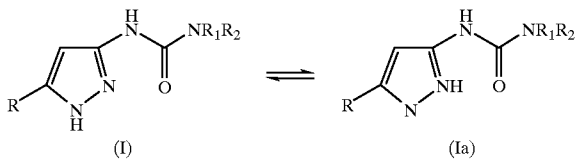

(I)                    (Ia)

In the following description, therefore, where only one tautomer is indicated for the compounds of formula (I), the other (Ia) is also intended as within the scope of the present invention.

In the present description, unless otherwise specified, with the term halogen atom includes a fluorine, chlorine, bromine or iodine atom.

As used herein and unless otherwise indicated, the terms alkyl and alkoxy include $C_1$–$C_6$ alkyl and $C_1$–$C_6$ alkoxy groups. The term straight or branched $C_1$–$C_6$ alkyl or $C_1$–$C_6$ alkoxy group includes a group selected from, methyl, ethyl, npropyl. isopropyl, n-butyl, isobutyl, sec-butyl, tertbutyl, n-pentyl, n-hexyl, methoxy, ethoxy, n-propoxy, isopropoxy, n-butoxy and the like.

Likewise, with the term alkylthio, alkylamino, dialkylamino, alkoxycarbonyl, alkoxycarbonylamino, alkylcarbonyl, alkylsulphonyl, alkoxycarbonyl, N-alkylpiperazinyl and the like, we intend any of the aforementioned groups wherein the alkyl and alkoxy moieties stand for $C_1$–$C_6$ alkyl or alkoxy groups.

Unless otherwise specified, with the term cycloalkyl includes a $C_3$–$C_6$ cycloalkyl group such as cyclopropyl, cyclobutyl, cyclopentyl and cyclohexyl as well as cycloalkyl and bridged cycloalkyl groups with up to 10 carbon atoms.

The term aryl stands for mono-, bi- or poly-carbocyclic or heterocyclic hydrocarbons with from 1 to 4 ring moieties, wherein at least one of the rings is aromatic, either fused or linked to each other by single bonds. These groups may have 5 to 20 carbon atoms, preferably 6 to 20 carbon atoms.

From the foregoing, one skilled in the art will readily appreciate that the term aryl also include aromatic heterocycles otherwise referred to as heteroaryl groups.

The term heterocycle refers to a 5 or 6 membered saturated or unsaturated carbocycle wherein one or more carbon atoms are replaced by one or more atoms selected from nitrogen, oxygen and sulphur. The number of heteroatoms is not limited and may be, for example, one, two, three, or more.

Example of aryl groups include phenyl, 1-naphtyl, 2-naphthyl, indanyl, indenyl, biphenyl, benzocycloalkyl, e.g. bicyclo[4.2.0]octa-1,3,5,-triene, benzoheterocyclyl, e.g. benzodioxolyl, quinolyl, isoquinolyl, quinoxalyl, indolyl, optionally benzocondensed pyrrolyl, furyl, thienyl, imidazolyl, pyrazolyl, thiazolyl, oxazolyl, isoxazolyl, pyridyl, pyrazinyl, pyrimidyl and the like.

Example of heterocycles are pyrrolidine, piperidine, piperazine, morpholine and the like.

The term $C_2$–$C_4$ alkenyl or alkynyl includes a group selected from vinyl, allyl, 1-propenyl, isopropenyl, 1-butenyl, 2-butenyl. 3-butenyl, ethynyl. propynyl, butynyl and the like.

The term oxo refers to a carbonyl (>C=O) group.

The term perfluorinated alkyl group includes a $C_1$–$C_4$ alkyl group further substituted by more than one fluorine atom such as, for instance, trifluoromethyl, 2,2,2-trifluoroethyl, 1,1,2,2,2-pentafluoroethyl and the like.

Pharmaceutically acceptable salts of the compounds of formula (I) include the acid addition salts with inorganic or organic, e.g., nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g., alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

The compounds of formula (I) may have asymmetric carbon atoms and may therefore exist either as racemic admixtures or as individual optical isomers.

Accordingly, the use as an antitumor agent of all the possible isomers and their admixtures and of both the metabolites and the pharmaceutically acceptable bioprecursors (otherwise referred to as pro-drugs) of the compounds of formula (I) are also within the scope of the present invention.

Preferred compounds of the invention of formula (I), are those where R is a $C_3$–$C_6$ cycloalkyl or an optionally substituted straight or branched $C_1$–$C_4$ alkyl group, a cycloalkyl or an aryl or arylalkyl group, and $R_1$ is a $C_1$–$C_4$ alkyl group or a phenyl, phenylalkyl, heteroaryl, heteroarylalkyl or heterocyclyl group, each being optionally substituted as defined above.

Still more preferred compounds, are those where R is a $C_3$–$C_6$ cycloalkyl and $R_1$ is a $C_1$–$C_4$ alkyl group substituted by hydroxy or amino, or is an aryl, arylalkyl, heterocyclyl or heterocyclylalkyl, wherein the aryl or heterocyclyl moiety is selected from the group consisting of phenyl or optionally benzocondensed pyiridine, indole, thiophene, thiazole, isoxazole, furan, piperidine, morpholine, each optionally further substituted.

Another class of preferred compounds of formula (I) are those where $R_1$ and $R_2$ form an optionally substituted heterocyclyl ring such as piperidino, piperazino or morpholino.

When the groups described above are substituted, the number of substituents is not particularly limited. For example, the groups described above may be substituted with, for example, one, two, three, or more of the substituents. Unless, otherwise indicated, the substituents may be the same or different, i.e., they are indepedently selected.

Examples of preferred compounds of the invention, which may be in the form of a pharmaceutically acceptable salt, e.g., hydrobromide or hydrochloride salt, include the following:

N-(3-cyclopropyl-1H-pyrazol-5-yl)-N'-[2-(1-piperidinyl) ethyl]urea;

4-[({[(3-cyclopropyl-1H-pyrazol-5yl)amino] carbonyl}amino)methyl]benzenesulfonamide;

N-(3-cyclopropyl-1H-pyrazol-5-yl)-N'-[2-(2-pyridinyl) ethyl]urea;

N-(3-cyclopropyl-1H-pyrazol-5-yl)-N'-[2-(1-pyrrolidinyl) ethyl]urea;

N-(3-chlorophenethyl)-N'-(3-cyclopropyl-1H-pyrazol-5-yl) urea;

N-(3-cyclopropyl-1H-pyrazol-5-yl)-N'-(2,3-dimethoxybenzyl)urea;

N-(3-cyclopropyl-1H-pyrazol-5-yl)-N'-(4-chlorobenzyl) urea;
N-[3-(tert-butyl)-1H-pyrazol-5-yl)]-N'-(4-piperidinylmethyl)urea;
N-[3-(tert-butyl)-1H-pyrazol-5-yl)]-N'-(3-fluorobenzyl) urea;
N-[3-(tert-butyl)-1H-pyrazol-5-yl)]-N'-(3,4-dimethoxybenzyl)urea;
N-[3-(tert-butyl)-1H-pyrazol-5-yl)]-N'-(4-chlorobenzyl) urea;
N-[3-(tert-butyl)-1H-pyrazol-5-yl)]-N'-(3,4-dihydroxybenzyl)urea;
N-[3-(tert-butyl)-1H-pyrazol-5-yl)]-N'-(3,4-dihethylbenzyl) urea;
N-[3-(tert-butyl)-1H-pyrazol-5-yl)]-N'-(3,-chlrophenethylbry)urea;
N-(3-cyclopropyl-1H-pyrazol-5-yl)-N'-(4-piperidinylmethyl)urea;
N-(3-cyclopropyl-1H-pyrazol-5-yl)-N'-(3-fluorobenzyl) urea;
N-(3-cyclopropyl-1H-pyrazol-5-yl)-N'-(3,4-dimethoxybenzyl)urea;
N-(3-cyclopropyl-1H-pyrazol-5-yl)-N'-(3,4-dimethylbenzyl)urea;
N-(3-cyclopropyl-1H-pyrazol-5-yl)-N'-(2-hydroxy-1-methyl-2-phenylethyl)urea;
N-(3-cyclopropyl-1H-pyrazol-5-yl)-N'-[(1-ethyl-2-pyrrolidiny)methyl]urea ;
N-(3-cyclopropyl-1H-pyrazol-5-yl)-N'-[2-(2H-imidazol-4-yl)ethyl]urea;
N-(3-cyclopropyl-1H-pyrazol-5-yl)-N'-[2-(5-methoxy-1H-indol-3-yl)ethyl]urea;
N-(3-cyclopropyl-1H-pyrazol-5-yl)-N'-(2H-indol-6-yl)urea;
N-(3-cyclopropyl-1H-pyrazol-5-yl)-N'-(1,3-benzodioxol-5-ylmethyl)urea;
N-(3-cyclopropyl-1H-pyrazol-5-yl)-N'-(2-(4-morpholinyl) ethyl]urea;
N-(3-cyclopropyl-1H-pyrazol-5-yl)-N'-(2-chlorobenzyl) urea;
N-(3-cyclopropyl-1H-pyrazol-5-yl)-N'-(2,4-dichlorobenzyl) urea;
N-(3-cyclopropyl-1H-pyrazol-5-yl)-N'-(2-ethoxybenzyl) urea;
N-(3-cyclopropyl-1H-pyrazol-5-yl)-N'-(3,4-dichlorobenzyl) urea;
N-(3-cyclopropyl-1H-pyrazol-5-yl)-N'-(3-methoxybenzyl) urea;
N-(3-cyclopropyl-1H-pyrazol-5-yl)-N'-(4-fluorobenzyl) urea;
N-(3-cyclopropyl-1H-pyrazol-5-yl)-N'-(3-trifluoromethylbenzyl)urea;
N-(3-cyclopropyl-1H-pyrazol-5-yl)-N'-(4-methylbenzyl) urea;
N-(3-cyclopropyl-1H-pyrazol-5-yl)-4-morpholinecarboxamide;
N-cyclobutyl-N'-(3-cyclopenthyl-1H-pyrazol-5-yl)urea;
N-(3-cyclopenthyl-1H-pyrazol-5-yl)-1-pyrrolidinecarboxamide;
4-(1,3-benzodioxol-5-ylmethyl)-N-(3-cyclopenthyl-1H-pyrazol-5-yl)-1-piperazinecarboxamide;
N-(3-cyclopentyl-1H-pyrazol-5-yl)-1-piperazinecarboxamide;
N-(3-cyclopentyl-1H-pyrazol-5-yl)-4-phenyl-1-piperazinecarboxamide;
N-(3-cyclopentyl-1H-pyrazol-5-yl)-4-methyl-1-piperazinecarboxamide;
N-(3-cyclopentyl-1H-pyrazol-5-yl)-4-benzyl-1-piperazinecarboxamide;
N-(3-cyclopentyl-1H-pyrazol-5-yl)-4-morpholinecarboxamide;
N-(3-cyclopentyl-1H-pyrazol-5-yl)-1-piperidinecarboxamide;
N-(3-cyclopentyl-1H-pyrazol-5-yl)-4-(aminomethyl)-1-piperidinecarboxamide;
N-(3-cyclopentyl-1H-pyrazol-5-yl)-N'-(1-benzyl-4-piperidinyl)urea;
N-(3-cyclopentyl-1H-pyrazol-5-yl)-N'-benzylurea;
N-(3-cyclopentyl-1H-pyrazol-5-yl)-N'-phenethylurea:
N-(3-cyclopentyl-1H-pyrazol-5-yl)-N'-(3,4-dimethoxyphenethyl)urea;
N-(3-cyclopentyl-1H-pyrazol-5-yl)-N'-(4-hydroxyphenethyl)urea;
N-(3-cyclopentyl-1H-pyrazol-5-yl)-N'-propylurea;
N-(3-cyclopentyl-1H-pyrazol-5-yl)-N'-(4-hydroxybutylurea;
N-(3-cyclopentyl-1H-pyrazol-5-yl)-4-[2-nitro-4-(trifluoromethyl)phenyl]-1-piperazinecarboxamide;
N-(3-phenethyl-1H-pyrazol-5-yl)-1-pyrrolidinecarboxamide;
4-(1,3-benzodioxol-5-yl-methyl)-N-(3-phenethyl-1H-pyrazol5-yl)-1-piperazinecarboxamide;
N-(3-phenethyl-1H-pyrazol-5-yl)-1-piperazinecarboxamide;
N-(3-phenethyl-1H-pyrazol-5-yl)-4-phenyl-1-piperazinecarboxamide;
N-(3-phenethyl-1H-pyrazol-5-yl)-4-methyl-1-piperazinecarboxamide;
N-(3-phenethyl-1H-pyrazol-5-yl)-4-benzyl-1-piperazinecarboxamide;
N-(3-phenethyl-1H-pyrazol-5-yl)-4-morpholinecarboxamide;
N-(3-phenethyl-1H-pyrazol-5-yl)-1-piperidinecarboxamide;
N-(3-phenethyl-1H-pyrazol-5-yl)-4-(aminomethyl)-1-piperidinecarboxamide;
N-(3-phenethyl-1H-pyrazol-5-yl)-N'-benzylurea;
N-(3-phenethyl-1H-pyrazol-5-yl)-N'-phenethylurea;
N-(3-phenethyl-1H-pyrazol-5-yl)-N'-(3,4-dimethoxyphenethyl)urea;
N-(3-phenethyl-1H-pyrazol-5-yl)-N'-(4-hydroxyphenethyl) urea;
N-(3-phenethyl-1H-pyrazol-5-yl)-N'-propylurea;
N-(3-phenethyl-1H-pyrazol-5-yl)-N'-(4-hydroxybutylurea;
N-(3-phenethyl-1H-pyrazol-5-yl)-4-[2-nitro-4-(trifluoromethyl)phenyl]-1-piperazinecarboxamide;
N-(3-cyclopropyl-1H-pyrazol-5-yl)-N'-butylurea;
N-(3-cyclopropyl-1H-pyrazol-5-yl)-N'-(2,4-dimethylphenyl)urea;
N-(3-cyclopropyl-1H-pyrazol-5-yl)-N'-(3,4-dimethoxyphenyl)urea;
N-(3-cyclopropyl-1H-pyrazol-5-yl)-N'-(3-carboxyphenyl) urea;
N-(3-cyclopropyl-1H-pyrazol-5-yl)-N'-(2,3-dimethylphenyl)urea;
N-(3-cyclopropyl-1H-pyrazol-5-yl)-N'-(3-carboxy-4-chlorophenyl)urea;
N-(3-cyclopropyl-1H-pyrazol-5-yl)-N'-(3,5-dimethylphenyl)urea;
N-(3-cyclopropyl-1H-pyrazol-5-yl)-N'-(3-carboxamidophenyl)urea;

N-(3-cyclopropyl-1H-pyrazol-5-yl)-N,-(3-carboxy-4-hydroxyphenyl)urea;
N-(3-cyclopropyl-1H-pyrazol-5-yl)-N'-(2,6-dimethylphenyl)urea;
N-(3-cyclopropyl-1H-pyrazol-5-yl)-N'-(4-cyanophenyl)urea;
N-(3-cyclopropyl-1H-pyrazol-5-yl)-N'-(3-acetylphenyl)urea;
N-(3-cyclopropyl-1H-pyrazol-5-yl)-N'-(1H-benzimidazol-6yl)urea;
N-(3-cyclopropyl-1H-pyrazol-5-yl)-N'-(4-hydroxy-3-methoxybenzyl)urea;
N-(3-cyclopropyl-1H-pyrazol-5-yl)-N'-benzylurea;
N-(3-cyclopropyl-1H-pyrazol-5-yl)-N'-{3-[3-(dimethylamino)-1-propynyl]phenyl}urea;
N-[3-({[(3-cyclopropyl-1H-pyrazol-5-yl)amino]carbonyl}amino)phenyl]methanesulfonamide;
2-[3-({[(3-cyclopropyl-1H-pyrazol-5-yl)amino]carbonyl}amino)anilino]acetamide;
N-(3-cyclopropyl-1H-pyrazol-5-yl)-N'-(2-hydroxyphenyl)urea;
N-(3-cyclopropyl-1H-pyrazol-5-yl)-N,-[3-(3-hydroxy-1-butynyl)phenyl]urea;
N-(3-cyclopropyl-1H-pyrazol-5-yl)-N'-(1H-indol-6-yl)urea;
N-(3-cyclopropyl-1H-pyrazol-5-yl)-N'-(1H-indol-5-yl)urea;
4-({[(3-cyclopropyl-1H-pyrazol-5-yl)amino]carbonyl}amino)benzenesulfonamide;
N-(3-cyclopropyl-1H-pyrazol-5-yl)-N'-(3-methoxyphenyl)urea;
N-(3-cyclopropyl-1H-pyrazol-5-yl)-N'-phenylurea;
N-[4-({[(3-cyclopropyl-1H-pyrazol-5-yl)amino]carbonyl}amino)phenyl]-N-methylacetamide;
N-(2-{[cyclohexyl(methyl)amino]methyl}phenyl)-N'-(3-cyclopropyl-1H-pyrazol-5-yl)urea;
N-(3-cyclopropyl-1H-pyrazol-5-yl)-N'-(2-methoxyphenyl)urea;
N-(3-cyclopropyl-1H-pyrazol-5-yl)-N'-(2-chlorophenyl)urea;
N-(3-cyclopropyl-1H-pyrazol-5-yl)-N'-(3-ethynylphenyl)urea;
N-(3-cyclopropyl-1H-pyrazol-5-yl)-N'-(4-aminophenyl)urea;
N-(3-cyclopropyl-1H-pyrazol-5-yl)-N'-(3-hydroxy-4-methylphenyl)urea;
N-(3-cyclopropyl-1H-pyrazol-5-yl)-3-oxo-3,4-dihydro-1(2H)-quinoxalinecarboxamide;
N-(3-cyclopropyl-1H-pyrazol-5-yl)-3,4-dihydro-2(1H)-isoquinolinecarboxamide;
N-(3-cyclopropyl-1H-pyrazol-5-yl)-N'-(4-pyridinylmethyl)urea;
N-(3-cyclopropyl-1H-pyrazol-5-yl)-N'-(2-furylmethyl)urea;
N-(3-cyclopropyl-1H-pyrazol-5-yl)-N'-(1,3-benzothiazol-5yl)urea;
N-(3-cyclopropyl-1H-pyrazol-5-yl)-N'-(1,3-dimethyl-1H-pyrazol-5-yl)urea;
N-[5-({[(3-cyclopropyl-1H-pyrazol-5-yl)amino]carbonyl}amino)-2-methoxyphenyl]acetamide;
N-[3-({[(3-cyclopropyl-1H-pyrazol-5-yl)amino]carbonyl}amino)-4-methoxyphenyl]acetamide;
N-(3-cyclopropyl-1H-pyrazol-5-yl)-N'-(3-aminophenyl)urea;
N-(3-cyclopropyl-1H-pyrazol-5-yl)-N'-(1H-imidazol-6yl)urea;
N-(3-cyclopropyl-1H-pyrazol-5-yl)-N'-(3-hydroxyphenyl)urea;
N-(3-cyclopropyl-1H-pyrazol-5-yl)-N'-(4-hydroxyphenyl)urea.

The compounds of formula (I) object of the present invention and the salts thereof can be obtained, for instance, by a process comprising:

(a) reacting a compound of formula (II):

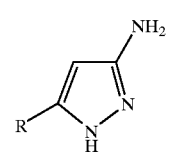

(II)

with a compound of formula (III):

R$_1$—NCO  (III)

wherein R and R$_1$ are as defined above, thus obtaining a compound of formula (IV):

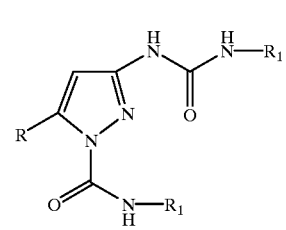

(IV)

wherein R and R$_1$ are as described above; and b) selectively hydrolyzing a compound of formula (IV) in a basic medium thus obtaining a compound of formula (I);: or, alternatively, a) reacting a compound of formula (V):

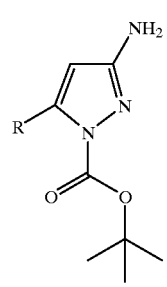

(V)

where R is described as above, with 4-nitrophenyl chloroformate, or a polymer supported form of it, thus obtaining a compound of formula (VI), or a polymer supported form of it (VI)

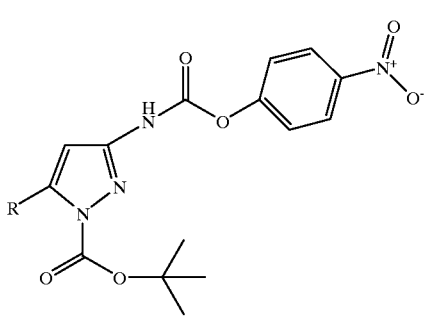

wherein R is defined as above;

(b) reacting a compound of formula (VI) with a compound of formula (VII):

R₁R₂NH                          (VII)

where $R_1$ and $R_2$ are defined as above, thus obtaining a compound of formula (VIII):

(VIII)

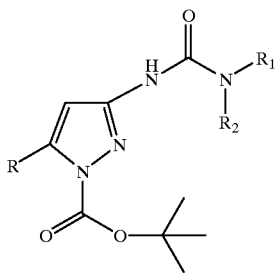

where R, $R_1$ and $R_2$ are defined as above, (c) hydrolyzing a compound of formula (VIII) in acidic medium thus obtaining compounds of formula (I); and, if desired, converting a 3-ureido-pyrazole derivative of formula (I) into another such derivative of formula (I), and/or into a salt thereof.

The compounds of formula (V) may be obtained by a process comprising:

(a) reacting a compound of formula (IX):

R—COOR₄                         (IX)

where R is as described above and $R_4$ is an alkyl group, with acetonitrile in the presence of basic agents thus obtaining a compound of formula (X):

R—CO—CH₂—CN                     (X)

where R is as described above;

(b) reacting a compound of formula (x) with hydrazine hydrate thus obtaining a compound of formula (II):

(II)

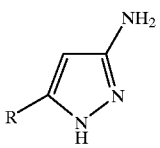

where R is as described above;

(b) oxidizing a compound of formula (II) thus obtaining a compound of formula (XI)

(XI)

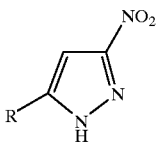

where R is as described above;

(c) reacting a compound of formula (XI) with terbutoxycarbonyl anhydride (Boc₂O) thus obtaining a compound of formula (XII):

(XII)

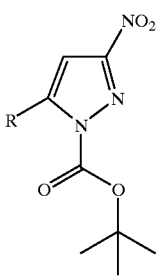

where R is as described above;

(e) reducing a compound of formula (XII) thus obtaining a compound of formula (V) where R is as described above.

The compounds of formula (I) may alternatively be obtained by a process comprising:

(a) reacting a compound of the above-described formula (II) with a compound of the above-described formula (III), thus obtaining a compound of formula (XIII):

(XIII)

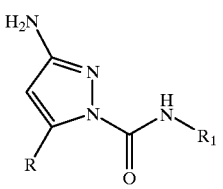

where R and $R_1$ are as described above;

(b) heating at reflux in the presence of sodium hydrate, methanol and an excess of a compound of formula (III), thus obtaining a compound of formula (I).

The compounds of formula (I) can alternatively be obtained by a process comprising:

(a) reacting a compound of formula (V):

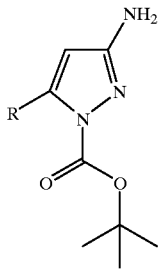

(V)

where R is as described above, with a compound of the above formula (III), thus obtaining a compound of formula (XIV):

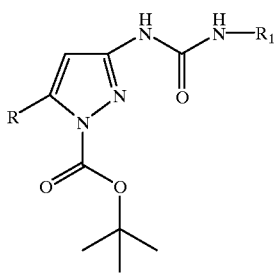

(XIV)

where R and $R_1$ are as described above;

(b) hydrolyzing a compound of formula (XIV) in an acidic medium thus obtaining a compound of formula (I), where R and $R_1$ are as described above.

The compounds of formula (I) can alternatively be obtained by a process comprising:

(a) reacting a compound of the above formula (V) with 1,1' carbonyldiimidazole thus obtaining compounds of formula (XV):

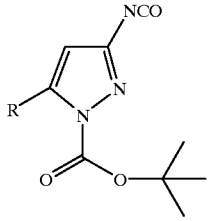

(XV)

where R is defined as above, (b) reacting a compound of formula (XV) with a compound of formula (VII):

 (VII)

where $R_1$ and $R_2$ are as above defined, thus obtaining a compound of formula (VIII)

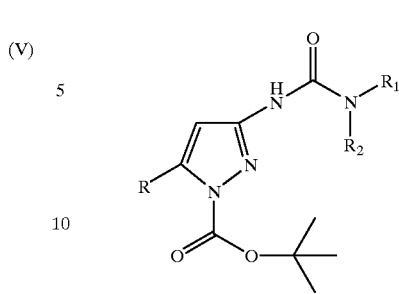

(VIII)

(c) hydrolizing a compound of formula (VIII) in acidic medium thus obtaining a compound of formula (I).

The compounds of formula (I) can alternatively be obtained by a process comprising:

(a) reacting the oxime resin (XVI) with triphosgene to give a polystyrene supported agent (XVII):

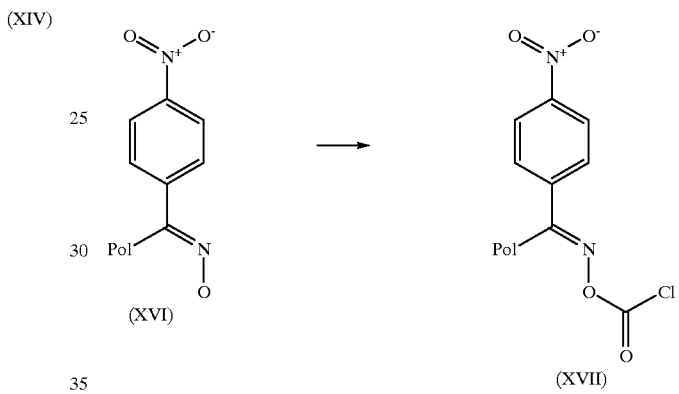

(b) reacting the compound (XVII) with a compound of the above-described formula (II), thus obtaining a compound of formula (XVIII), where R is as described above;

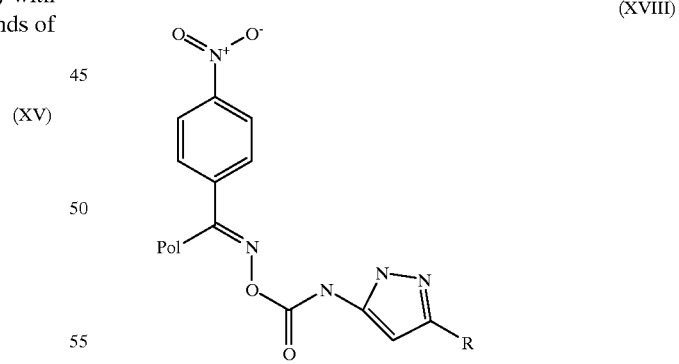

(XVIII)

(c) reacting the compound of formula (XVIII) with a compound of the above-described formula (VII), thus obtaining the compound of formula (I), where R, $R_1$ and $R_2$ are as described above.

As will be readily appreciated by one skilled in the art, if the compound of formula (I), prepared according to the above process is obtained as an admixture of isomers, its separation into the single isomers of formula (I) according to conventional techniques is within the scope of the present invention.

Likewise, the conversion into the free compound (I) of a corresponding salt thereof, according to well-known procedures in the art, is within the scope of the invention.

The process described above may be conducted analogous to to well-known methods.

The reaction between a compound of formula (II) or formula (V) and a compound of formula (III) can be carried out in the presence of sodium hydrogen carbonate or a tertiary base, such as triethylamine, N-methylmorpholine, N,N-diisopropylethylamine or pyridine, in a suitable solvent such as toluene, dichloromethane, chloroform, diethylether, tetrahydrofuran, acetonitrile, dioxane or N,N-dimethylformamide, at a temperature ranging from about 10° C. to reflux.

The reaction of a compound of formula (IV) to give a compound of formula (I) can be carried out with a base such as sodium hydroxide, potassium hydroxide, sodium carbonate or potassium carbonate in a suitable solvent such as a mixture of methanol or ethanol and water at room temperature.

The reaction of the compounds of formula (II) and the compounds of formula (III) to give the compounds of formula (XIII) can be carried out with a base such as sodium hydrogencarbonate or sodium hydrate in suitable solvent such as ethanol or methanol at room temperature.

The reaction of the compounds of formula (XIII) to give the compounds of formula (I) can be carried out by heating at a temperature ranging from 60 to 80° C. in presence of an excess of compounds of formula (III) in presence of a base such as sodium hydrate in a suitable solvent such as methanol or ethanol.

The reaction of a compound of formula (XIV) to give a compound of formula (I) can be carried out with an acid such as trifluoroacetic acid, hydrochloric acid, formic acid, in a suitable solvent such as methylene chloride at a temperature ranging from −10° C. to room temperature.

The reaction of a compound of formula (IX) to give a compound of formula (X) may be carried out with acetonitrile and a base such as sodium hydride in a suitable solvent such as diethylether, tetrahydrofaran, dioxane at a temperature ranging from room temperature to 120° C.

The reaction of a compound of formula (X) to give a compound of formula (II) may be carried out with hydrazine hydrate, in a solvent such as methanol or ethanol at a temperature ranging from room temperature to 80° C.

The reaction of a compound of formula (II) to give a compound of formula (XI) may be carried out with oxone® (potassium peroxymonosulfate) or another oxidizing agent such as hydrogen peroxide in a suitable solvent such as a mixture of water-acetone at a temperature ranging from 0° C. to room temperature.

The reaction of a compound of formula (XI) to give a compound of formula (XII) may be carried out with terbutoxycarbonyl anhydride in a suitable solvent such as a mixture of methylene chloride-water at room temperature, in the presence of sodium hydrogen carbonate.

The reaction of a compound of formula (XII) to give a compound of formula (V) may be carried out directly with hydrogen in presence of a catalyst such as palladium on charcoal in a suitable solvent such as methanol or ethanol at room temperature.

The reaction of a compound of formula (V) to give a compound of formula (VI) may be carried out with 4-nitrophenyl chloroformate or a polymer supported form of it in the presence of a tertiary base such as triethylamine, N-methylmorpholine, N,N-diisopropylethylamine or pyridine, in a suitable solvent such as toluene, dichloromethane, chloroform, diethylether, tetrahydrofuran, acetonitrile, dioxane or N,N-dimethylformamide, at a temperature ranging from about −10° C. to room temperature.

The reaction between a compound of formula (VI) or (XV) and a compound of formula (VII) to give a compound of formula (VIII) can be carried out in a suitable solvent such as toluene, dichloromethane, chloroform, diethylether, tetrahydrofuran, acetonitrile, dioxane or N,N-dimethylformamide, at a temperature ranging from about room temperature to reflux.

The reaction of a compound of formula (VIII) to give a compound of formula (I) can be carried out with an acid such as trifluoroacetic acid, hydrochloric acid, formic acid, in a suitable solvent such as methylene chloride at a temperature ranging from −10° C. to room temperature.

The reaction of a compound of formula (V) to give a compound of formula (XV) can be carried out with 1,1'-carbonyldiimidazole, bis(trichloromethyl)carbonate or trichloromethyl chloroformate in the presence, if necessary, of a tertiary base such as triethyl amine, N,N-diisopropylethylamine or pyridine, in a suitable solvent such as dichloromethane, chloroform, toluene, dioxane or tetrahydrofuran at a temperature ranging from 0° C. to reflux.

The reaction of the oxime resin (XVI) with triphosgene to give the compound of formula (XVII) can be carried out in a suitable solvent such as dichloromethane at room temperature.

The reaction of the compound of formula (XVII) with the compound of formula (II) to give a compound of formula (XVIII) can be carried out in a suitable solvent such as dichloromethane at room temperature.

The reaction of the compounds of formula (XVIII) with the compounds of formula (VII) to give the compounds of formula (I) can be carried out in a suitable solvent such as toluene, dichloromethane, chloroform, diethylether, tetrahydrofuran, acetonitrile, dioxane or N,N-dimethylformamide at a temperature ranging from room temperature to reflux.

Also the optional conversion of a compound of formula (I) into another compound of formula (I) can be carried out according to known methods.

The optional salification of a compound of formula (I) or the conversion of a salt into the free compound as well as the separation of a mixture of isomers into the single isomers may be carried out by conventional methods.

The compounds of formula (III), (VII), (IX) and (X) are known commercially available products or can be obtained according to conventional synthetic methods.

When preparing the compounds of formula (I) according to the process object of the present invention, optional functional groups within both the starting materials or the intermediates thereof, which could give rise to unwanted side reactions, need to be properly protected according to conventional techniques.

Likewise, the conversion of these latter into the free deprotected compounds may be carried out according to known procedures.

As will be readily appreciated by one skilled in the art, the above process for preparing the compounds of formula (I) may be used to prepare another compound of formula (I) which also include known compounds.

Pharmacoloy

The compounds of formula (I) are active as cdk/cyclin inhibitors as they gave positive results when tested according to the following procedure.

The inhibiting activity of putative cdk/cyclin inhibitors and the potency of selected compounds was determined through a method of assay based on the use of the MultiScreen-PH 96 well plate (Millipore), in which a phosphocellulose filter paper was placed at each well bottom allowing binding of positive charged substrate after a washing/filtration step.

When a radioactivity labeled phosphate moiety was transferred by the ser/threo kinase to the filter-bound histone, light emitted was measured in a scintillation counter.

The inhibition assay of cdk2/Cyclin A activity was performed according to the following protocol:

Kinase Reaction 1.5.M histone H1 substrate, 25.M ATP (0.5 uCi P33g-ATP), 100 ng Cyclin A/cdk2 complex, 10.M inhibitor in a final volume of 100.1 buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20.1 EDTA 120 mM.

Capture 100.1 were transferred from each well to MultiScreen plate, to allow substrate binding to phosphocellulose filter. Plates were then washed 3 times with 150.1/well PBS Ca++/Mg++ free and filtered by MultiScreen filtration system.

Detection

Filters were allowed to dry at 37° C., then 100.1/well scintillant were added and 33P labeled histone H1 was detected by radioactivity counting in the Top-Count instrument.

Results

Data were analyzed and expressed as % inhibition referred to total activity of enzyme (=100%).

All compounds showing inhibition >50% were further analyzed in order to study and define the kinetic-profile of inhibitor through Ki calculation.

The protocol used was the same described above, except for ATP and substrate concentrations. Either the concentration of ATP and histone H1 substrate were varied: 4, 8, 12, 24, 48.M for ATP (containing proportionally diluted P33g-ATP) and 0.4, 0.8, 1.2, 2.4, 4.8.M for histone were used in absence and presence of two different, properly chosen inhibitor concentrations.

Experimental data were analyzed by the computer program "SigmaPlot" for Ki determination, using a random bireactant system equation:

$$v = \frac{V\max \frac{(A)(B)}{aKAKB}}{1 + \frac{(A)}{KA} + \frac{(B)}{KB} + \frac{(A)(B)}{aKAKB}}$$

where A=ATP and B=histone H1.

In addition, the inhibiting activity of putative cdk/cyclin inhibitors and the potency of selected compounds was determined through a method of assay based on the use of a SPA (Scintillation Proximity Assay) 96 well plate assay. The assay is based on the ability of streptavidin coated SPA beads to capture a biotinylated peptide derived from a phosphorylation site of histone.

When a radioactivity labeled phosphate moiety was transferred by the ser/threo kinase to the biotinylated histone peptide, light emitted was measured in a scintillation counter.

The inhibition assay of cdk5/p25 activity was performed according to the following protocol:

Kinase Reaction 1.0.M biotinylated histone peptide substrate, 0.25 uCi P33g-ATP, 4 nNM cdk2/p25 complex, 0–100.M inhibitor in a final volume of 100.1 buffer (Hepes 20 mM pH 7.5, $MgCl_2$ 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 uM ATP and 5 mM EDTA. The beads were allowed to settle, and the radioactivity incorporated in the 33P-labeled peptide was detected in a Top Count scintillation counter.

Results

Data were analyzed and expressed as % Inhibition using the formula:

$$100X(1-(\text{Unknown}-\text{Bkgd})/(\text{Enz. Control}-\text{Bkgd}))$$

$IC_{50}$ values were calculated using a variation of the four parameter logistics equation:

$$Y=100/[1+10 \char`\^(\text{Log}EC50-X)*\text{Slope})]$$

Where X=log(uM) and Y=% Inhibition.

The compounds of formula (I) are therefore useful to restrict the unregulated proliferation of tumor cells, hence in therapy in the treatment of various tumors such as, for instance, carcinomas, e.g., mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The compounds of the present invention can be administered either as single agents or, alternatively, in combination with known anticancer treatments such as radiation therapy or chemotherapy regimen in combination with cytostatic or cytotoxic agents.

As an example, the above compounds can be administered in combination with one or more chemotherapeutic agents such as, for instance, taxane, taxane derivatives, CPT-11, camptothecin derivatives, anthracycline glycosides, e.g. doxorubicin or epirubicin, etoposide, navelbine, vinblastine, carboplatin, cisplatin and the like, optionally within liposomal formulations thereof.

The compounds of formula (I) of the present invention, suitable for administration to a mammal, e.g., to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arable gum, gelatins, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tableting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty acid ester surfactant or lecithin.

EXAMPLES

Having generally described this invention, a further understanding can be obtained by reference to certain specific examples which are provided herein for purposes of illustration only and are not intended to be limiting unless otherwise specified.

Example 1

N-(3-cyclopropyl-1H-pyrazol-5-yl)-N'-phenylurea

To 0.4 g (3.2 mmol) of 3-cyclopropyl-5-amino-1H-pyrazole in 10 ml of 95% ethanol containing 0.3 g of sodium hydrogencarbonate 0.35 ml (3 mmol) of phenylisocyanate were added dropwise over several minutes. After 30 min water was added, and the solid was filtered, washed with 10% HCl and then with water. The filtrate was concentrated in vacua. The crude was recrystallized from methanol/water to give white peddles of 5-amino-3-cyclopropyl-N-phenyl-1H-pyrazole-l-carboxamide, m.p. 97–99° C.;

MS (EI) m/z (rel. intensity) 242 ($M^+$, 13), 123 (99), 119 (86), 96 (74), 91 (86), 80 (85), 77 (53), 65 (61), 64 (79), 63 (52), 51 (51).

To 5-amino-3-cyclopropyl-N-phenyl-1H-pyrazole-l-carboxamide (0.5 g, 2 mmol) in 6 ml of methanol 0.5 ml (4.6 mmol) of phenylisocyanate and 2 ml of 10% NaOH were added. The mixture was refluxed for about 2h, then cooled, quenched with 10% HCl and extracted with ethyl acetate. The organic phase was washed with 10% HCl, water and brine. Concentration and chromatography on silica gel, eluting with 8% to 20% acetone in methylene chloride, afforded 100 mg (20% yield) of N-(3-cyclopropyl-1H-pyrazol-5-yl)-N'-phenylurea as a colorless, glassy solid.

m.p. 162–164° C.;

$^1$H NMR (DMSO-$d_6$) δ12.0 (s, 1H), 9.2 (s, 1H), 8.84 (s, 1H), 7.42 (app.d, 2H), 7.27 (app.t, 2H), 6.96 (app.t, 1H), 5.86 (s, 1H), 1.85 (m, 1H), 0.91 (m, 2H), 0.67 (m, 2H);

MS (EI) m/z (rel. intensity) 242 ($M^+$, 9), 149 (43), 123 (89), 122 (38), 119 (89), 93 (99), 91 (54), 80 (46), 66 (47), 65 (40), 64 (34).

Example 2

N-(3-cyclopropyl-1H-pyrazol-5-yl)-N'-(2,4-dichlorobenzyl)urea 1 g (8.13 mmol) of 3-cyclopropyl-5-amino-1H-pyrazole are dissolved in 10 ml of ethanol containing 1.37 g (16.26 mmol) of sodium hydrogen carbonate and 3.27 g (16.26 mmol) of 2,4-dichlorobenzyl isocyanate. After 3 hours at room temperature 50 ml of water were added and the solid was filtered. The filtrate was evaporated to dryness and then redissolved with 10 ml of methanol. 8.2 ml of 1M sodium hydrate were added and the mixture stirred 4 h at room temperature. Methanol is evaporated and the residue is dissolved with dichloromethane and washed with water. The organic layer was dried over anhydrous sodium sulfate and concentrated in vacuo to afford 1.5 g (60% yield) of the title compound.

m.p. 177–179° C.;

$^1$H NMR (DMSO-$d_6$) δ11.9 (s, 1H), 8.84 (s, 1H), 7.60 (d, 1H), 7.55 (br s, 1H), 7.43 (dd, 1H), 7.36 (d, 1H), 5.67 (s, 1H), 4.36 (d, 2H), 1.81 (m, 1H), 0.89 (m, 2H), 0.61 (m, 2H);

HRMS (FAB) calcd for $C_{14}H_{14}Cl_2N_4O+H$ 325.0623, found 325.0621.

Example 3

3-Cyclopropyl-3-oxo-propanenitrile 4.5 g (0.15 mol) of sodium hydride 80% were suspended in 200 ml of dioxane, 7.5 ml of acetonitrile (0.15 mol) were dropped and, after 20 minutes, a solution of ethyl cyclopropancarboxylate (0.125 mol) in 100 ml of the same solvent was added. The mixture was maintained at reflux for 3 hours, under stirring, then 400 ml of water were added and the unreacted starting material extracted with methylene chloride. The aqueous layer was acidified with diluted hydrochloric acid and extracted with the same solvent. The organic layer was dried over anhydrous sodium sulfate and evaporated to dryness to give a residue that, after column chromatography (cyclohexane-ethylacetate), afforded 7.8 g (57% yield) of the title compound.

$^1$H NMR (400 MHZ, $CDCl_3$) δ3.59 (s, 2H), 2.12 (dddd, 1H, J=7.6, 7.6, 4.5, 4.5), 1.21 (m, 2H), 1.10 (m, 2H).

EI-MS: m/z 69 (85, M-$C_3H_5$.); m/z 39 (100, $C_3H_5^+$).

Example 4

3-Cyclopropyl-5-amino-1H-pyrazole 5 g (0.046 mol) of 3-cyclopropyl-3-oxo-propanenitrile were dissolved in 200 ml of ethanol and 2.26 ml (0.046 mol) of hydrazine hydrate were added. The solution was maintained at reflux for 5 hours and then the solvent evaporated under vacuum. The residue was redissolved with methylene chloride and washed several times with brine. The organic layer was dried over anhydrous sodium sulfate and the solvent evaporated to give 4.53 g (80% yield) of the title compound.

¹H NMR (400 MHZ, CDCl₃) δ6–7 (b, 3H, NH+NH₂), 5.02 (s, 1H), 1.68 (dddd, 1H, J=8.3, 8.3, 4.9, 4.9), 0.76 (m, 2H), 0.54 (m, 2H).

ESI (+) MS: m/z 124 (100, MH⁺).

Example 5
3-Cyclopropyl-5-nitro-1H-pyrazole

To a solution of 2.7 g of sodium hydrate in 454 ml of water 7.1 g (0.058 mol) of 3-cyclopropyl-5-amino-1H-pyrazole and 46.5 g of sodium hydrogenocarbonate were added at 0° C. After 10 minutes a solution of 337 ml of acetone in 221 ml of water and a solution of 130 g (0.21 mol) of oxone in 580 ml of water were contemporarly dropped under vigorous stirring. After 4 hours at the same temperature the reaction is quenched with a saturated solution of sodium sulfite and extracted with ethylacetate. The organic layer was dried over anhydrous sodium sulfate and evaporated to dryness to give 4.6 g (52% yield) of the title compound.

¹H NMR (400 MHZ, CDCl₃) δ6.51 (s, 1H), 2.01 (dddd, 1H, J=8.2, 8.2, 5.1, 5.1), 1.10 (m, 2H), 0.79 (m, 2H).

EI-MS: m/z 153 (100, M⁺.); 136 (60, M-OH.).

Example 6
Tert-butyl-3-nitro-5-cyclopropyl-1H-pyrazole-1-carboxylate 4.9 g (0.032 mol) of 3-cyclopropyl-5-nitro-1H-pyrazole were dissolved in 200 ml of methylene chloride and 200 ml of a saturated solution of sodium hydrogenocarbonate were added. 35 g (0.16 mol) of terbutoxycarbonyl anhydride were then added under stirring at room temperature. After 24 hours the layers were separated and the organic one dried over sodium sulfate and evaporated under vacuum. The residue was chromatographed on a silica gel column (cyclohexane-ethylacetate) to give 7.7 g (95% yield) of the title compound.

¹H NMR (400 MHZ, CDCl₃) δ6.49 (s, 1H), 2.48 (dddd, 1H, J=8.5, 8.5, 5.3, 5.3), 1.68 (s, 9H), 1.13 (m, 2H), 0.78 (m, 2H).

ESI (+) MS: m/z 276 (100, MNa⁺); 220 [60, (MNa-C₄H₈)⁺].

Example 7
Tert-butyl-3-amino-5-cyclopropyl-1H-pyrazole-1-carboxylate 1.2 g (4.74 mmol) of tert-butyl-3-nitro-5-cyclopropyl-1H-pyrazole-1-carboxylate were dissolved in 20 ml of ethanol and hydrogenated in presence of 200 mg of palladium on charcoal 10% at 50 psi and room temperature to give, after filtration on celite and evaporation of the solvent, 0.96 g (95% yield) of the title compound.

¹H NMR (400 MHZ, CDCl₃) δ5.39 (s, 1H), 3.82 (br s, 2H) 2.34 (dddd, 1H, J=8.4, 8.4, 5.2, 5.2), 1.63 (s, 9H), 0.97 (m, 2H), 0.64 (m, 2H).

ESI (+) MS: m/z 246 (20, MNa⁺); 168 [100, (MH-C₄H₈)⁺]; 124 [90, (MH-C₅H₈O₂)⁺].

Example 8
Preparation of Polymer Supported Agent (XVIII)

To a solution of 1.067 g (loading 0.57 mmol/g, 0.608 mmol) of oxime resin (XVI) in 10 ml of dichloromethane 241 mg (0.811 mmol) of triphosgene in 5 ml of the same solvent were added. The reaction was agitated overnight. The resin was collected on a scintered glass funnel and washed well with dichloromethane. Drying the residue in the vacuum oven afforded 1.085 g of resin. Analysis of the resin by FT-IR showed a strong carbonyl stretch at 1800 cm⁻¹. The resin was then resuspended in 10 ml of dichloromethane and 232 mg (1.88 mmol) of 3-cyclopropyl-5-aminopyrazole were added. After 12 hours under stirring the resin was collected by filtration and washed with methanol. After drying in the vacuum oven, 1.097 g of resin were obtained. Analysis by FT-IR showed a strong carbonyl stretch at 1761 cm⁻¹.

Example 9
N-(3-cyclopropyl-1H-pyrazol-5-yl)-N'-(3-methoxybenzyl) urea 100 mg (0.1 mmol) of oxime-carbamate resin (XVIII) was suspended in 1 ml of DMSO and 11 mg (0.08 mmol) of 3-methoxybenzylamine in 0.2 M DMSO solution were added. The reaction was heated at 80° C. for three hours, then the resin was separated by filtration, washed with 150 μl of dichloromethane and 150 μl of MeOH. The filtrate was concentrated to give, after trituration with diethylether 11.4 mg (50% yield) of the title compound.

Analogously the following compounds can be prepared:

N-(3-cyclopropyl-1H-pyrazol-5-yl)-N'-[(1-ethyl-2-pyrrolidinyl)methyl]urea;
N-(3-cyclopropyl-1H-pyrazol-5-yl)-N'-[2-(2H-imidazol-4-yl)ethyl]urea;
N-(3-cyclopropyl-1H-pyrazol-5-yl)-N'-[2-(5-methoxy-2H-indol-3-yl)ethyl]urea;
N-(3-cyclopropyl-1H-pyrazol-5-yl)-N'-(1H-indol-6-yl)urea;
N-(3-cyclopropyl-1H-pyrazol-5-yl)-N'-[2-(4-morpholinyl) ethyl]urea;
N-(3-cyclopropyl-1H-pyrazol-5-yl)-N'-(2-chlorobenzyl) urea;
N-(3-cyclopropyl-1H-pyrazol-5-yl)-N'-(2,4-dichlorobenzyl) urea;
N-(3-cyclopropyl-1H-pyrazol-5-yl)-N'-(2-ethoxybenzyl) urea;
N-(3-cyclopropyl-1H-pyrazol-5-yl)-N'-(3,4-dichlorobenzyl) urea;
N-(3-cyclopropyl-1H-pyrazol-5-yl)-N'-(3-trifluoromethylbenzyl)urea;
N-(3-cyclopropyl-1H-pyrazol-5-yl)-N'-(4-fluorobenzyl) urea;
N-(3-cyclopropyl-1H-pyrazol-5-yl)-N'-(4-methylbenzyl) urea;
N-(3-cyclopropyl-1H-pyrazol-5-yl)-N'-(4-chlorobenzyl) urea;
N-(3-chlorophenethyl)-N'-(3-cyclopropyl-1H-pyrazol-5-yl) urea;
N-(3-cyclopropyl-1H-pyrazol-5-yl)-N'-[2-(2-pyridinyl) ethyl]urea;
N-(3-cyclopropyl-1H-pyrazol-5-yl)-N'-[2-(1-pyrrolidinyl) ethyl]urea;
N-(3-cyclopropyl-1H-pyrazol-5-yl)-N'-butylurea;
N-(3-cyclopropyl-1H-pyrazol-5-yl)-N'-[2-(1-piperidinyl) ethyl]urea;
4-[({[(3-cyclopropyl-1H-pyrazol-5-yl)amino] carbonyl}amino)methyl]benzensulfonamide;
N-(3-cyclopentyl-1H-pyrazol-5-yl)-4-[2-nitro-4-(trifluoromethyl)phenyl]-1-piperazinecarboxamide;
N-(3-cyclopentyl-1H-pyrazol-5-yl)-N'-propylurea;
N-(3-cyclopentyl-1H-pyrazol-5-yl)-N'-(4-hydroxybutyl) urea;
N-(3-cyclopentyl-1H-pyrazol-5-yl)-N'-(3,4-dimethoxyphenethyl)urea;
N-(3-cyclopenty-1H-pyrazol-5-yl)-N'-(4-hydroxyphenethyl)urea;
N-(3-cyclopentyl-1H-pyrazol-5-yl)-N'-benzylurea;
N-(3-cyclopentyl-1H-pyrazol-5-yl)-N'-phenethylurea;
N-(3-cyclopentyl-1H-pyrazol-5-yl)-N,-(1-benzyl-4-piperidinyl)urea;

N-(3-cyclopentyl-1H-pyrazol-5-yl)-1-piperidinecarboxamide;
N-(3-cyclopentyl-1H-pyrazol-5-yl)-4-(aminomethyl)-1-piperidinecarboxamide;
N-(3-cyclopentyl-1H-pyrazol-5-yl)-4-benzyl-1-piperazinecarboxamide;
N-(3-cyclopentyl-1H-pyrazol-5-yl)-4-morpholinecarboxamide;
N-(3-cyclopentyl-1H-pyrazol-5-yl)-4-phenyl-1-piperazinecarboxamide;
N-(3-cyclopentyl-1H-pyrazol-5-yl)-4-methyl-1-piperazinecarboxamide;
N-(3-cyclopentyl-1H-pyrazol-5-yl)-1-piperazinecarboxamide;
N-(3-cyclopentyl-1H-pyrazol-5-yl)-4-(1,3-benzodioxol-5-yl-methyl)-1-piperazinecarboxamide;
N-(3-cyclopentyl-1H-pyrazol-5-yl)-N'-cyclobutylurea;
N-(cyclopentyl-1H-pyrazol-5-yl)-1-pyrrolidinecarboxamide;
N-cyclobutyl-N'-(3-phenethyl-1H-pyrazol-5-yl)urea;
N-(3-phenethyl-1H-pyrazol-5-yl)-1-pyrrolidinecarboxamide;
4-(1,3-benzodioxol-5-yl-methyl)-N-(3-phenethyl-1H-pyrazol-5-yl)-1-piperazinecarboxamide;
N-(3-phenethyl-1H-pyrazol-5-yl)-1-piperazinecarboxamide;
N-(3-phenethyl-1H-pyrazol-5-yl)-4-phenyl-1-piperazinecarboxamide;
N-(3-phenethyl-1H-pyrazol-5-yl)-4-methyl-1-piperazinecarboxamide;
N-(3-phenethyl-1H-pyrazol-5-yl)-4-benzyl-1-piperazinecarboxamide;
N-(3-phenethyl-1H-pyrazol-5-yl)-4-morpholinecarboxamide;
N-(3-phenethyl-1H-pyrazol-5-yl)-1-piperidinecarboxamide;
N-(3-phenethyl-1H-pyrazol-5-yl)-4-(aminomethyl)-1-piperidinecarboxamide;
N-(3-phenethyl-1H-pyrazol-5-yl)-N'-(1-benzyl-4-piperidinyl)urea;
N-(3-phenethyl-1H-pyrazol-5-yl)-N,-benzylurea;
N-(3-phenethyl-1H-pyrazol-5-yl)-N'-phenethylurea;
N-(3-phenethyl-1H-pyrazol-5-yl)-N'-(3,4-dimethoxyphenethyl)urea;
N-(3-phenethyl-1H- pyrazol-5-yl)- N'-(4-hydroxyphenethyl)urea;
N-(3-phenethyl-1H-pyrazol-5-yl)-N'-propylurea;
N-(3-phenethyl-1H-pyrazol-5-yl)-N'-(4-hydroxybutylurea;
N-(3-phenethyl-1H-pyrazol-5-yl)-4-[2-nitro-4-(trifluoromethyl)phenyl]-1-piperazinecarboxamide;

All compounds were characterized by mass spectrometry (MS). LC-MS confirmed that in each case the principle component had a molecular ion corresponding to the expected product. The compounds showed an HPLC area % ranging from 70 to 100.

HPLC Analysis
Solvent A: $H_2O/CH_3CN=90/10+0.1\%$ TFA
Solvent B: $H_2O/CH_3CN=10/90+0.075\%$ TFA

| Time (min) | % A | % B |
|---|---|---|
| 0 | 0 | 100 |
| 6.5 | 0 | 100 |
| 7 | 100 | 0 |
| 10 | 100 | 0 |

Rate: 1.5 ml/min
Detection: UV 254 nm
Temperature: room temperature
Column: Supelco™, Discovery RP Amide C16, sum, (50× 4.6)mm Example 10
N-(3-cycloipropyl-1H:pyrazol-5-yl)-N'-(1,3-benzodioxol-5-yl-methyl)urea To a solution of 1.5 g (6.7 mmol) of tert-butyl-3-amino-5-cyclopropyl-1H-pyrazole-1-carboxylate in 15 ml of dichloromethane under nitrogen 1.41 g (7 mmol) of p-nitrophenylchloroformate in a mixture of 7 ml of dichloromethane and 1 ml of pyridine were added dropwise at 0° C. After 12 hours at room temperature the precipitate was separated by filtration to give 1.95 g (75% yield) of p-nitrophenyl-tert-butyl-3-amino-5-cyclopropyl-carbamate. This intermediate (5 mmol), without further purification, was suspended in 20 ml of acetonitrile and 830 mg (5.5 mmol) of (1,3-benzodioxol-5-yl)-methylamine were added. After 3 hours at 80° C. the suspension was filtered and the filtrate concentrated in vacua. The residue was redissolved in ethylacetate and washed with a saturated solution of sodium hydrogencaibonate and then with water. The organic layer was dried over anhydrous sodium sulfate and evaporated to dryness. The crude was purified by chromatography on a silica gel column (hexane/ethylacetate 7/3) to give 1.2 g (60% yield) of N-(3-cyclopropyl-1-tert-butoxycarbonyl-pyrazol-5-yl)-N'-(1,3-benzodioxol-5-yl-methyl)urea. At last the previous intermediate (3 mmol) was dissolved in 25 ml of a mixture 10% v/v of trifluoroacetic acid-dichloromethane. After 1 hour at room temperature, the solvent was evaporated to dryness the residue redissolved with dichloromethane and washed with a saturated solution of sodium hydrogencarbonate. The organic layer was dried over anhydrous sodium sulfate and concentrated to give 855 mg (95% yield) of the title compound.

Obviously, numerous modifications and variations of the present invention are possible in light of the above teachings. It is therefore to be understood that within the scope of the appended claims, the invention may be practiced otherwise than as specifically described herein.

What is claimed is:
1. A 3-ureido-pyrazole compound represented by formula (I):

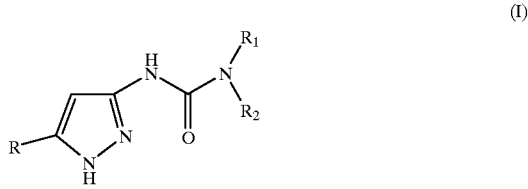

wherein
R is a $C_3$–$C_6$ cycloalkyl group optionally substituted with a straight or branched $C_1$–$C_6$ alkyl group or is a $C_1$–$C_6$ alkyl or arylalkyl group, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

$R_1$ is —$(CH_2)_n$—$R_3$;

n is 0 or an integer from 1 to 4;

$R_3$ is hydrogen, hydroxy, amino, or a group selected from the group consisting of cycloalkyl, aryl and heterocyclyl, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

wherein said heterocyclyl is selected from the group consisting of benzodioxolyl, quinolyl, isoquinolyl, quinoxalyl, indolyl, optionally benzocondensed pyrrolyl, furanyl, thienyl, imidazolyl, pyrazolyl, thiazolyl, oxazolyl, isoxazolyl, pyridyl, pyrazinyl, pyrimidyl, pyrrolidinyl, piperidinyl, benzocondensed pyiridinyl, piperazinyl, thiophenyl, and morpholinyl;

$R_2$ is hydrogen, or $R_2$ and $R_1$, together with the nitrogen atom to which they are bonded, form a group selected from the group consisting of piperidino, piperazino and morpholino, and said group selected from the group consisting of piperidino, piperazino and morpholino is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

or a pharmaceutically acceptable salt thereof;

provided that when n is 0 and $R_2$ is hydrogen, R is a $C_3$–$C_6$ cycloalkyl group optionally substituted with a straight or branched $C_1$–$C_6$ alkyl group.

2. The 3-ureido-pyrazole compound of claim 1, wherein

R is a $C_3$–$C_6$ cycloalkyl or an optionally substituted straight or branched $C_1$–$C_4$ alkyl group or an arylalkyl group;

$R_1$ is a group selected from the group consisting of $C_1$–$C_4$ alkyl, phenyl, phenylalkyl, benzodioxolyl, quinolyl, isoquinolyl, quinoxalyl, indolyl, optionally benzocondensed pyrrolyl, furanyl, thienyl, imidazolyl, pyrazolyl, thiazolyl, oxazolyl, isoxazolyl, pyridyl, pyrazinyl, pyrimidyl, pyrrolidinyl, piperidinyl, benzocondensed pyiridinyl, piperazinyl, thiophenyl, and morpholinyl; and said group selected from the group consisting of $C_1$–$C_4$ alkyl, phenyl, phenylalkyl, benzodioxolyl, quinolyl, isoquinolyl, quinoxalyl, indolyl, optionally benzocondensed pyrrolyl, furanyl, thienyl, imidazolyl, pyrazolyl, thiazolyl, oxazolyl, isoxazolyl, pyridyl, pyrazinyl, pyrimidyl, pyrrolidinyl, piperidinyl, benzocondensed pyiridinyl, piperazinyl, thiophenyl, and morpholinyl; is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents or a pharmaceutically acceptable salt thereof.

3. The 3-ureido-pyrazole compound of claim 2, wherein

R is a $C_3$–$C_6$ cycloalkyl group;

$R_1$ is a $C_1$–$C_4$ alkyl group substituted by hydroxy or amino, or is an aryl, arylalkyl, heterocyclyl or heterocyclylalkyl, wherein the aryl or heterocyclyl moiety is selected from the group consisting of phenyl or optionally benzocondensed pyiridine, indole, thiophene, thiazole, isoxazole, furane, piperidine, morpholine, each optionally further substituted;

or a pharmaceutically acceptable salt thereof.

4. The 3-ureido-pyrazole compound of claim 1, wherein $R_1$ and $R_2$, together with the nitrogen atom to which they are bonded, form an optionally substituted piperidino, piperazino or morpholino ring.

5. The 3-ureido-pyrazole compound of claim 1, wherein R is a cyclopropyl group.

6. The 3-ureido-pyrazole compound of claim 1, wherein R is a cyclopentyl group.

7. The 3-ureido-pyrazole compound of claim 1, wherein R is a cyclohexyl group.

8. The 3-ureido-pyrazole compound of claim 1, wherein R is a $C_3$–$C_6$ cycloalkyl group optionally substituted with a straight or branched $C_1$–$C_6$ alkyl group.

9. The 3-ureido-pyrazole compound of claim 1, which is selected from the group consisting of N-(3-cyclopropyl-1H-pyrazol-5-yl)-N'-[2-(1-piperidinyl)ethyl]urea;

4-[({[(3-cyclopropyl-1H-pyrazol-5-yl)amino]carbonyl}amino)methyl]benzenesulfonamide;

N-(3-cyclopropyl-1H-pyrazol-5-yl)-N'-[2-(2-pyridinyl)ethyl]urea;

N-(3-cyclopropyl-1H-pyrazol-5-yl)-N'-[2-(1-pyrrolidinyl)ethyl]urea;

N-(3-cyclopropyl-1H-pyrazol-5-yl)-N'-(2,3-dimethoxybenzyl)urea;

N-(3-cyclopropyl-1H-pyrazol-5-yl)-N'-(4-chlorobenzyl)urea;

N-(3-cyclopropyl-1H-pyrazol-5-yl)-N'-(4-piperidinylmethyl)urea;

N-(3-cyclopropyl-1H-pyrazol-5-yl)-N'-(3-fluorobenzyl)urea;

N-(3-cyclopropyl-1H-pyrazol-5-yl)-N'-(3,4-dimethoxybenzyl)urea;

N-(3-cyclopropyl-1H-pyrazol-5-yl)-N'-(3,4-dimethylbenzyl)urea;

N-(3-cyclopropyl-1H-pyrazol-5-yl)-N'-(2-hydroxy-1-methyl-2-phenylethyl)urea;

N-(3-cyclopropyl-1H-pyrazol-5-yl)-N'-[(1-ethyl-2-pyrrolidinyl)methyl]urea;
N-(3-cyclopropyl-1H-pyrazol-5-yl)-N'-[2-(2H-imidazol-4-yl)ethyl]urea;
N-(3-cyclopropyl-1H-pyrazol-5-yl))-N'-[2-(5-methoxy-1H-indol-3-yl)ethyl]urea;
N-(3-cyclopropyl-1H-pyrazol-5-yl)-N'-(1,3-benzodioxol-5-ylmethyl)urea;
N-(3-cyclopropyl-1H-pyrazol-5-yl)-N'-(2-(4-morpholinyl)ethyl]urea;
N-(3-cyclopropyl-1H-pyrazol-5-yl)-N'-(2-chlorobenzyl)urea;
N-(3-cyclopropyl-1H-pyrazol-5-yl)-N'-(2,4-dichlorobenzyl)urea;
N-(3-cyclopropyl-1H-pyrazol-5-yl)-N'-(2-ethoxybenzyl)urea;
N-(3-cyclopropyl-1H-pyrazol-5-yl)-N'-(3,4-dichlorobenzyl)urea;
N-(3-cyclopropyl-1H-pyrazol-5-yl)-N'-(3-methoxybenzyl)urea;
N-(3-cyclopropyl-1H-pyrazol-5-yl)-N'-(4-fluorobenzyl)urea;
N-(3-cyclopropyl-1H-pyrazol-5-yl)-N'-(3-trifluoromethylbenzyl)urea;
N-(3-cyclopropyl-1H-pyrazol-5-yl)-N'-(4-methylbenzyl)urea
N-(3-cyclopropyl-1H-pyrazol-5-yl)-N'-(4-hydroxy-3-methoxybenzyl)urea;
N-(3-cyclopropyl-1H-pyrazol-5-yl)-N'-benzylurea
N-(3-cyclopropyl-1H-pyrazol-5-yl)-N'-(4-pyridinylmethyl)urea;
N-(3-cyclopropyl-1H-pyrazol-5-yl)-N'-(2-furylmethyl)urea; and
pharmaceutically acceptable salts thereof.

10. The 3-ureido-pyrazole compound of claim 1, which is selected from the group consisting of
N-(3-cyclopropyl-1H-pyrazol-5-yl)-N'-(1H-indol-6-yl)urea;
N-(3-cyclopropyl-1H-pyrazol-5-yl)-4-morpholinecarboxamide;
N-(3-cyclopropyl-1H-pyrazol-5-yl)-N'-butylurea;
N-(3-cyclopropyl-1H-pyrazol-5-yl)-N'-(1H-benzimidazol-6yl)urea;
N-[3-({[(3-cyclopropyl-1H-pyrazol-5-yl)amino]carbonyl}amino)phenyl]methanesulfonamide;
2-[3-({[(3-cyclopropyl-1H-pyrazol-5-yl)amino]carbonyl}amino)anilino]acetamide;
N-(3-cyclopropyl-1H-pyrazol-5-yl)-N'-(1H-indol-6-yl)urea;
N-(3-cyclopropyl-1H-pyrazol-5-yl)-N'-(1H-indol-5-yl)urea;
4-({[(3-cyclopropyl-1H-pyrazol-5-yl)amino]carbonyl}amino)benzenesulfonamide
N-(3-cyclopropyl-1H-pyrazol-5-yl)-3-oxo-3,4-dihydro-1(2H)-quinoxalinecarboxamide;
N-(3-cyclopropyl-1H-pyrazol-5-yl)-3,4-dihydro-2(1H)-isoquinolinecarboxamide;
N-(3-cyclopropyl-1H-pyrazol-5-yl)-N'-(1,3-benzothiazol-5yl)urea;
N-(3-cyclopropyl-1H-pyrazol-5-yl)-N'-(1,3-dimethyl-1H-pyrazol-5-yl)urea;
N-[5-({[(3-cyclopropyl-1H-pyrazol-5-yl)amino]carbonyl}amino)-2-methoxyphenyl]acetamide;
N-[3-({[(3-cyclopropyl-1H-pyrazol-5-yl)amino]carbonyl}amino)-4-methoxyphenyl]acetamide;
N-(3-cyclopropyl-1H-pyrazol-5-yl)-N'-(1H-imidazol-6yl)urea;
N-(3-chlorophenethyl)-N'-(3-cyclopropyl-1H-pyrazol-5-yl)urea; and
pharmaceutically acceptable salts thereof.

11. The 3-ureido-pyrazole compound of claim 1, which is selected from the group consisting of
N-(3-cyclopropyl-1H-pyrazol-5-yl)-N'-(2,4-dimethylphenyl)urea;
N-(3-cyclopropyl-1H-pyrazol-5-yl)-N'-(3,4-dimethoxyphenyl)urea;
N-(3-cyclopropyl-1H-pyrazol-5-yl)-N'-(3-carboxyphenyl)urea;
N-(3-cyclopropyl-1H-pyrazol-5-yl)-N'-(2,3-dimethylphenyl)urea;
N-(3-cyclopropyl-1H-pyrazol-5-yl)-N'-(3-carboxy-4-chlorophenyl)urea;
N-(3-cyclopropyl-1H-pyrazol-5-yl)-N'-(3,5-dimethylphenyl)urea;
N-(3-cyclopropyl-1H-pyrazol-5-yl)-N'-(3-carboxamidophenyl)urea;
N-(3-cyclopropyl-1H-pyrazol-5-yl)-N,-(3-carboxy-4-hydroxyphenyl)urea;
N-(3-cyclopropyl-1H-pyrazol-5-yl)-N'-(2,6-dimethylphenyl)urea;
N-(3-cyclopropyl-1H-pyrazol-5-yl)-N'-(4-cyanophenyl)urea;
N-(3-cyclopropyl-1H-pyrazol-5-yl)-N'-(3-acetylphenyl)urea;
N-(3-cyclopropyl-1H-pyrazol-5-yl)-N'-{3-[3-(dimethylamino)-1-propynyl]phenyl}urea;
N-(3-cyclopropyl-1H-pyrazol-5-yl)-N'-(2-hydroxyphenyl)urea;
N-(3-cyclopropyl-1H-pyrazol-5-yl)-N,-[3-(3-hydroxy-1-butynyl)phenyl]urea;
N-(3-cyclopropyl-1H-pyrazol-5-yl)-N'-(3-methoxyphenyl)urea;
N-(3-cyclopropyl-1H-pyrazol-5-yl)-N'-phenylurea;
N-[4-({[(3-cyclopropyl-1H-pyrazol-5-yl)amino]carbonyl}amino)phenyl]-N-methylacetamide;
N-(2-{[cyclohexyl(methyl)amino]methyl}phenyl)-N'-(3-cyclopropyl-1H-pyrazol-5-yl)urea;
N-(3-cyclopropyl-1H-pyrazol-5-yl)-N'-(2-methoxyphenyl)urea;
N-(3-cyclopropyl-1H-pyrazol-5-yl)-N'-(2-chlorophenyl)urea;
N-(3-cyclopropyl-1H-pyrazol-5-yl)-N'-(3-ethynylphenyl)urea;
N-(3-cyclopropyl-1H-pyrazol-5-yl)-N'-(4-aminophenyl)urea;
N-(3-cyclopropyl-1H-pyrazol-5-yl)-N'-(3-hydroxy-4-methylphenyl)urea;
N-(3-cyclopropyl-1H-pyrazol-5-yl)-N'-(3-aminophenyl)urea;
N-(3-cyclopropyl-1H-pyrazol-5-yl)-N'-(3-hydroxyphenyl)urea;
N-(3-cyclopropyl-1H-pyrazol-5-yl)-N'-(4-hydroxyphenyl)urea; and
pharmaceutically acceptable salts thereof.

12. The 3-ureido-pyrazole compound of claim 1, which is selected from the group consisting of
N-cyclobutyl-N'-(3-cyclopentyl-1H-pyrazol-5-yl)urea;
N-(3-cyclopentyl-1H-pyrazol-5-yl)-1-pyrrolidinecarboxamide;
4-(1,3-benzodioxol-5-ylmethyl)-N-(3-cyclopentyl-1H-pyrazol-5-yl)-1-piperazinecarboxamide;
N-(3-cyclopentyl-1H-pyrazol-5-yl)-1-piperazinecarboxamide;
N-(3-cyclopentyl-1H-pyrazol-5-yl)-4-phenyl-1-piperazinecarboxamide;
N-(3-cyclopentyl-1H-pyrazol-5-yl)-4-methyl-1-piperazinecarboxamide;

N-(3-cyclopentyl-1H-pyrazol-5-yl)-4-benzyl-1-piperazinecarboxamide;
N-(3-cyclopentyl-1H-pyrazol-5-yl)-4-morpholinecarboxamide;
N-(3-cyclopentyl-1H-pyrazol-5-yl)-1-piperidinecarboxamide;
N-(3-cyclopentyl-1H-pyrazol-5-yl)-4-(aminomethyl)-1-piperidinecarboxamide;
N-(3-cyclopentyl-1H-pyrazol-5-yl)-N'-(1-benzyl-4-piperidinyl)urea;
N-(3-cyclopentyl-1H-pyrazol-5-yl)-N'-benzylurea;
N-(3-cyclopentyl-1H-pyrazol-5-yl)-N'-phenethylurea:
N-(3-cyclopentyl-1H-pyrazol-5-yl)-N'-(3,4-dimethoxyphenethyl)urea;
N-(3-cyclopentyl-1H-pyrazol-5-yl)-N'-(4-hydroxyphenethyl)urea;
N-(3-cyclopentyl-1H-pyrazol-5-yl)-N'-propylurea;
N-(3-cyclopentyl-1H-pyrazol-5-yl)-N'-(4-hydroxybutylurea;
N-(3-cyclopentyl-1H-pyrazol-5-yl)-4-[2-nitro-4-(trifluoromethyl)phenyl]-1-piperazinecarboxamide; and
pharmaceutically acceptable salts thereof.

13. The 3-ureido-pyrazole compound of claim 1, which is selected from the group consisting of
N-[3-(tert-butyl)-1H-pyrazol-5-yl)]-N'-(4-piperidinylmethyl)urea;
N-[3-(tert-butyl)-1H-pyrazol-5-yl)]-N'-(3-fluorobenzyl)urea;
N-[3-(tert-butyl)-1H-pyrazol-5-yl)]-N'-(3,4-dimethoxybenzyl)urea;
N-[3-(tert-butyl)-1H-pyrazol-5-yl)]-N'-(4-chlorobenzyl)urea;
N-[3-(tert-butyl)-1H-pyrazol-5-yl)]-N'-(3,4-dihydroxybenzyl)urea;
N-[3-(tert-butyl)-1H-pyrazol-5-yl)]-N'-(3,4-dimethylbenzyl)urea;
N-[3-(tert-butyl)-1H-pyrazol-5-yl)]-N'-(3-chlorophenethyl)urea; and
pharmaceutically acceptable salts thereof.

14. The 3-ureido-pyrazole compound of claim 1, which is selected from the group consisting of
N-(3-phenethyl-1H-pyrazol-5-yl)-1-pyrrolidinecarboxamide;
4-(1,3-benzodioxol-5-yl-methyl)-N-(3-phenethyl-1H-pyrazol5-yl)-1-piperazinecarboxamide;
N-(3-phenethyl-1H-pyrazol-5-yl)-1-piperazinecarboxamide;
N-(3-phenethyl-1H-pyrazol-5-yl)-4-phenyl-1-piperazinecarboxamide;
N-(3-phenethyl-1H-pyrazol-5-yl)-4-methyl-1-piperazinecarboxamide;
N-(3-phenethyl-1H-pyrazol-5-yl)-4-benzyl-1-piperazinecarboxamide;
N-(3-phenethyl-1H-pyrazol-5-yl)-4-morpholinecarboxamide;
N-(3-phenethyl-1H-pyrazol-5-yl)-1-piperidinecarboxamide;
N-(3-phenethyl-1H-pyrazol-5-yl)-4-(aminomethyl)-1-piperidinecarboxamide;
N-(3-phenethyl-1H-pyrazol-5-yl)-N'-benzylurea;
N-(3-phenethyl-1H-pyrazol-5-yl)-N'-phenethylurea;
N-(3-phenethyl-1H-pyrazol-5-yl)-N'-(3,4-dimethoxyphenethyl)urea;
N-(3-phenethyl-1H-pyrazol-5-yl)-N'-(4-hydroxyphenethyl)urea;
N-(3-phenethyl-1H-pyrazol-5-yl)-N'-propylurea;
N-(3-phenethyl-1H-pyrazol-5-yl)-N'-(4-hydroxybutylurea;
N-(3-phenethyl-1H-pyrazol-5-yl)-4-[2-nitro-4-(trifluoromethyl)phenyl]-1-piperazinecarboxamide; and
pharmaceutically acceptable salts thereof.

15. A pharmaceutical composition, comprising a 3-ureido-pyrazole compound represented by formula (I):

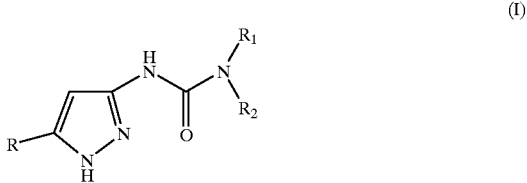

wherein
R is a $C_3$–$C_6$ cycloalkyl group optionally substituted with a straight or branched $C_1$–$C_6$ alkyl group or is a $C_1$–$C_6$ alkyl or arylalkyl group, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

$R_1$ is —$(CH_2)_n$—$R_3$;

n is 0 or an integer from 1 to 4;

$R_3$ is hydrogen, hydroxy, amino, or a group selected from the group consisting of cycloalkyl, aryl and heterocyclyl, which is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

wherein said heterocyclyl is selected from the group consisting of benzodioxolyl, quinolyl, isoquinolyl, quinoxalyl, indolyl, optionally benzocondensed pyrrolyl, furanyl, thienyl, imidazolyl, pyrazolyl, thiazolyl, oxazolyl, isoxazolyl, pyridyl, pyrazinyl, pyrimidyl, pyrrolidinyl, piperidinyl, benzocondensed pyiridinyl, piperazinyl, thiophenyl, and morpholinyl;

$R_2$ is hydrogen, or $R_2$ and $R_1$, together with the nitrogen atom to which they are bonded, form a group selected from the group consisting of piperidino, piperazino and morpholino, and said group selected from the group consisting of piperidino, piperazino and morpholino is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N- alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents;

or a pharmaceutically acceptable salt thereof;

provided that when n is 0 and $R_2$ is hydrogen, R is a $C_3$–$C_6$ cycloalkyl group optionally substituted with a straight or branched $C_1$–$C_6$ alkyl group, and least one pharmaceutically acceptable carrier and/or diluent.

16. The pharmaceutical composition of claim 15, wherein R is a $C_3$–$C_6$ cycloalkyl or an optionally substituted straight or branched $C_1$–$C_4$ alkyl group or an arylalkyl group;

$R_1$ is a group selected from the group consisting of $C_1$–$C_4$ alkyl, phenyl, phenylalkyl, benzodioxolyl, quinolyl, isoquinolyl, quinoxalyl, indolyl, optionally benzocondensed pyrrolyl, furanyl, thienyl, imidazolyl, pyrazolyl, thiazolyl, oxazolyl, isoxazolyl, pyridyl, pyrazinyl, pyrimidyl, pyrrolidinyl, piperidinyl, benzocondensed pyiridinyl, piperazinyl, thiophenyl, and morpholinyl; and said group selected from the group consisting of $C_1$–$C_4$ alkyl, phenyl, phenylalkyl, benzodioxolyl, quinolyl, isoquinolyl, quinoxalyl, indolyl, optionally benzocondensed pyrrolyl, furanyl, thienyl, imidazolyl, pyrazolyl, thiazolyl, oxazolyl, isoxazolyl, pyridyl, pyrazinyl, pyrimidyl, pyrrolidinyl, piperidinyl, benzocondensed pyiridinyl, piperazinyl, thiophenyl, and morpholinyl; is optionally substituted with one or more hydroxy, halogen, nitro, cyano, oxo, carboxy, amino, alkylamino, dialkylamino, alkylcarbonylamino, alkoxycarbonylamino, alkoxycarbonylalkylamino, aminocarbonylalkylamino, N-alkyl-N-carbonylamino, N-cycloalkyl-N-alkylaminoalkyl, aminoalkyl, aminocarbonyl, alkyl, cycloalkyl, alkylthio, alkoxy, alkylcarbonyl, alkylsulphonyl, alkylsulphonylamino, aminosulphonyl, alkoxycarbonyl, aryl, arylalkyl, aryloxy, arylthio, arylsulphonyl, arylamino, arylcarbonyl, N-alkyl-piperazinyl, 4-morpholinyl, perfluorinated $C_1$–$C_4$ alkyl, $C_2$–$C_4$ alkenyl, $C_2$–$C_4$ alkynyl, $C_2$–$C_4$ aminoalkynyl or $C_2$–$C_4$ hydroxyalkynyl substituents or a pharmaceutically acceptable salt thereof.

17. The pharmaceutical composition of claim 15, wherein R is a $C_3$–$C_6$ cycloalkyl group;

$R_1$ is a $C_1$–$C_4$ alkyl group substituted by hydroxy or amino, or is an aryl, arylalkyl, heterocyclyl or heterocyclylalkyl, wherein the aryl or heterocyclyl moiety is selected from the group consisting of phenyl or optionally benzocondensed pyiridine, indole, thiophene, thiazole, isoxazole, furane, piperidine, morpholine, each optionally further substituted;

or a pharmaceutically acceptable salt thereof.

18. The pharmaceutical composition of claim 15, wherein $R_1$ and $R_2$, together with the nitrogen atom to which they are bonded, form an optionally substituted piperidino, piperazino or morpholino ring.

19. The pharmaceutical composition of claim 15, wherein R is a cyclopropyl group.

20. The pharmaceutical composition of claim 15, wherein R is a cyclopentyl group.

21. The pharmaceutical composition of claim 15, wherein R is a cyclohexyl group.

22. The pharmaceutical composition of claim 15, wherein R is a $C_3$–$C_6$ cycloalkyl group optionally substituted with a straight or branched $C_1$–$C_6$ alkyl group.

23. The pharmaceutical composition of claim 15, which is selected from the group consisting of N-(3-cyclopropyl-1H-pyrazol-5-yl)-N'-[2-(1-piperidinyl)ethyl]urea;

4-[({[(3-cyclopropyl-1H-pyrazol-5-yl)amino]carbonyl}amino)methyl]benzenesulfonamide;

N-(3-cyclopropyl-1H-pyrazol-5-yl)-N'-[2-(2-pyridinyl)ethyl]urea;

N-(3-cyclopropyl-1H-pyrazol-5-yl)-N'-[2-(1-pyrrolidinyl)ethyl]urea;

N-(3-cyclopropyl-1H-pyrazol-5-yl)-N'-(2,3-dimethoxybenzyl)urea;

N-(3-cyclopropyl-1H-pyrazol-5-yl)-N'-(4-chlorobenzyl)urea;

N-(3-cyclopropyl-1H-pyrazol-5-yl)-N'-(4-piperidinylmethyl)urea;

N-(3-cyclopropyl-1H-pyrazol-5-yl)-N'-(3-fluorobenzyl)urea;

N-(3-cyclopropyl-1H-pyrazol-5-yl)-N'-(3,4-dimethoxybenzyl)urea;

N-(3-cyclopropyl-1H-pyrazol-5-yl)-N'-(3,4-dimethylbenzyl)urea;

N-(3-cyclopropyl-1H-pyrazol-5-yl)-N'-(2-hydroxy-1-methyl-2-phenylethyl)urea;

N-(3-cyclopropyl-1H-pyrazol-5-yl)-N'-[(1-ethyl-2-pyrrolidinyl)methyl]urea;

N-(3-cyclopropyl-1H-pyrazol-5-yl)-N'-[2-(2H-imidazol-4-yl)ethyl]urea;

N-(3-cyclopropyl-1H-pyrazol-5-yl)-N'-[2-(5-methoxy-1H-indol-3-yl)ethyl]urea;

N-(3-cyclopropyl-1H-pyrazol-5-yl)-N'-(1,3-benzodioxol-5-ylmethyl)urea;

N-(3-cyclopropyl-1H-pyrazol-5-yl)-N'-(2-(4-morpholinyl)ethyl]urea;

N-(3-cyclopropyl-1H-pyrazol-5-yl)-N'-(2-chlorobenzyl)urea;

N-(3-cyclopropyl-1H-pyrazol-5-yl)-N'-(2,4-dichlorobenzyl)urea;

N-(3-cyclopropyl-1H-pyrazol-5-yl)-N'-(2-ethoxybenzyl)urea;

N-(3-cyclopropyl-1H-pyrazol-5-yl)-N'-(3,4-dichlorobenzyl)urea;

N-(3-cyclopropyl-1H-pyrazol-5-yl)-N'-(3-methoxybenzyl)urea;

N-(3-cyclopropyl-1H-pyrazol-5-yl)-N'-(4-fluorobenzyl)urea;

N-(3-cyclopropyl-1H-pyrazol-5-yl)-N'-(3-trifluoromethylbenzyl)urea;

N-(3-cyclopropyl-1H-pyrazol-5-yl)-N'-(4-methylbenzyl)urea

N-(3-cyclopropyl-1H-pyrazol-5-yl)-N'-(4-hydroxy-3-methoxybenzyl)urea;

N-(3-cyclopropyl-1H-pyrazol-5-yl)-N'-benzylurea

N-(3-cyclopropyl-1H-pyrazol-5-yl)-N'-(4-pyridinylmethyl)urea;

N-(3-cyclopropyl-1H-pyrazol-5-yl)-N'-(2-flurylmethyl)urea; and pharmaceutically acceptable salts thereof.

24. The pharmaceutical composition of claim 15, which is selected from the group consisting of N-(3-cyclopropyl-1H-pyrazol-5-yl)-N'-(1H-indol-6-yl)urea;

N-(3-cyclopropyl-1H-pyrazol-5-yl)-4-morpholinecarboxamide;

N-(3-cyclopropyl-1H-pyrazol-5-yl)-N'-butylurea;

N-(3-cyclopropyl-1H-pyrazol-5-yl)-N'-(1H-benzimidazol-6yl)urea;
N-[3-({[(3-cyclopropyl-1H-pyrazol-5-yl)amino]carbonyl}amino)phenyl]methanesulfonamide;
2-[3-({[(3-cyclopropyl-1H-pyrazol-5-yl)amino]carbonyl}amino)anilino]acetamide;
N-(3-cyclopropyl-1H-pyrazol-5-yl)-N'-(1H-indol-6-yl)urea;
N-(3-cyclopropyl-1H-pyrazol-5-yl)-N'-(1H-indol-5-yl)urea;
4-({[(3-cyclopropyl-1H-pyrazol-5-yl)amino]carbonyl}amino)benzenesulfonamide
N-(3-cyclopropyl-1H-pyrazol-5-yl)-3-oxo-3,4-dihydro-1(2H)-quinoxalinecarboxamide;
N-(3-cyclopropyl-1H-pyrazol-5-yl)-3,4-dihydro-2(1H)-isoquinolinecarboxamide;
N-(3-cyclopropyl-1H-pyrazol-5-yl)-N'-(1,3-benzothiazol-5yl)urea;
N-(3-cyclopropyl-1H-pyrazol-5-yl)-N'-(1,3-dimethyl-1H-pyrazol-5-yl)urea;
N-[5-({[(3-cyclopropyl-1H-pyrazol-5-yl)amino]carbonyl}amino)-2-methoxyphenyl]acetamide;
N-[3-({[(3-cyclopropyl-1H-pyrazol-5-yl)amino]carbonyl}amino)-4-methoxyphenyl]acetamide;
N-(3-cyclopropyl-1H-pyrazol-5-yl)-N'-(1H-imidazol-6yl)urea;
N-(3-chlorophenethyl)-N'-(3-cyclopropyl-1H-pyrazol-5-yl)urea; and
pharmaceutically acceptable salts thereof.

25. The pharmaceutical composition of claim 15, which is selected from the group consisting of
N-(3-cyclopropyl-1H-pyrazol-5-yl)-N'-(2,4-dimethylphenyl)urea;
N-(3-cyclopropyl-1H-pyrazol-5-yl)-N'-(3,4-dimethoxyphenyl)urea;
N-(3-cyclopropyl-1H-pyrazol-5-yl)-N'-(3-carboxyphenyl)urea;
N-(3-cyclopropyl-1H-pyrazol-5-yl)-N'-(2,3-dimethylphenyl)urea;
N-(3-cyclopropyl-1H-pyrazol-5-yl)-N'-(3-carboxy-4-chlorophenyl)urea;
N-(3-cyclopropyl-1H-pyrazol-5-yl)-N'-(3,5-dimethylphenyl)urea;
N-(3-cyclopropyl-1H-pyrazol-5-yl)-N'-(3-carboxamidophenyl)urea;
N-(3-cyclopropyl-1H-pyrazol-5-yl)-N,-(3-carboxy-4-hydroxyphenyl)urea;
N-(3-cyclopropyl-1H-pyrazol-5-yl)-N'-(2,6-dimethylphenyl)urea;
N-(3-cyclopropyl-1H-pyrazol-5-yl)-N'-(4-cyanophenyl)urea;
N-(3-cyclopropyl-1H-pyrazol-5-yl)-N'-(3-acetylphenyl)urea;
N-(3-cyclopropyl-1H-pyrazol-5-yl)-N'-{3-[3-(dimethylamino)-1-propynyl]phenyl}urea;
N-(3-cyclopropyl-1H-pyrazol-5-yl)-N'-(2-hydroxyphenyl)urea;
N-(3-cyclopropyl-1H-pyrazol-5-yl)-N,-[3-(3-hydroxy-1-butynyl)phenyl]urea;
N-(3-cyclopropyl-1H-pyrazol-5-yl)-N'-(3-methoxyphenyl)urea;
N-(3-cyclopropyl-1H-pyrazol-5-yl)-N'-phenylurea;
N-[4-({[(3-cyclopropyl-1H-pyrazol-5-yl)amino]carbonyl}amino)phenyl]-N-methylacetamide;
N-(2-{[cyclohexyl(methyl)amino]methyl}phenyl)-N'-(3-cyclopropyl-1H-pyrazol-5-yl)urea;
N-(3-cyclopropyl-1H-pyrazol-5-yl)-N'-(2-methoxyphenyl)urea;
N-(3-cyclopropyl-1H-pyrazol-5-yl)-N'-(2-chlorophenyl)urea;
N-(3-cyclopropyl-1H-pyrazol-5-yl)-N'-(3-ethynylphenyl)urea;
N-(3-cyclopropyl-1H-pyrazol-5-yl)-N'-(4-aminophenyl)urea;
N-(3-cyclopropyl-1H-pyrazol-5-yl)-N'-(3-hydroxy-4-methylphenyl)urea;
N-(3-cyclopropyl-1H-pyrazol-5-yl)-N'-(3-aminophenyl)urea;
N-(3-cyclopropyl-1H-pyrazol-5-yl)-N'-(3-hydroxyphenyl)urea;
N-(3-cyclopropyl-1H-pyrazol-5-yl)-N'-(4-hydroxyphenyl)urea; and
pharmaceutically acceptable salts thereof.

26. The pharmaceutical composition of claim 15, which is selected from the group consisting of
N-cyclobutyl-N'-(3-cyclopentyl-1H-pyrazol-5-yl)urea;
N-(3-cyclopentyl-1H-pyrazol-5-yl)-1-pyrrolidinecarboxamide;
4-(1,3-benzodioxol-5-ylmethyl)-N-(3-cyclopentyl-1H-pyrazol-5-yl)-1-piperazinecarboxamide;
N-(3-cyclopentyl-1H-pyrazol-5-yl)-1-piperazinecarboxamide;
N-(3-cyclopentyl-1H-pyrazol-5-yl)-4-phenyl-1-piperazinecarboxamide;
N-(3-cyclopentyl-1H-pyrazol-5-yl)-4-methyl-1-piperazinecarboxamide;
N-(3-cyclopentyl-1H-pyrazol-5-yl)-4-benzyl-1-piperazinecarboxamide;
N-(3-cyclopentyl-1H-pyrazol-5-yl)-4-morpholinecarboxamide;
N-(3-cyclopentyl-1H-pyrazol-5-yl)-1-piperidinecarboxamide;
N-(3-cyclopentyl-1H-pyrazol-5-yl)-4-(aminomethyl)-1-piperidinecarboxamide;
N-(3-cyclopentyl-1H-pyrazol-5-yl)-N'-(1-benzyl-4-piperidinyl)urea;
N-(3-cyclopentyl-1H-pyrazol-5-yl)-N'-benzylurea;
N-(3-cyclopentyl-1H-pyrazol-5-yl)-N'-phenethylurea:
N-(3-cyclopentyl-1H-pyrazol-5-yl)-N'-(3,4-dimethoxyphenethyl)urea;
N-(3-cyclopentyl-1H-pyrazol-5-yl)-N'-(4-hydroxyphenethyl)urea;
N-(3-cyclopentyl-1H-pyrazol-5-yl)-N'-propylurea;
N-(3-cyclopentyl-1H-pyrazol-5-yl)-N'-(4-hydroxybutylurea;
N-(3-cyclopentyl-1H-pyrazol-5-yl)-4-[2-nitro-4-(trifluoromethyl)phenyl]-1-piperazinecarboxamide; and
pharmaceutically acceptable salts thereof.

27. The pharmaceutical composition of claim 15, which is selected from the group consisting of
N-[3-(tert-butyl)-1H-pyrazol-5-yl)]-N'-(4-piperidinylmethyl)urea;
N-[3-(tert-butyl)-1H-pyrazol-5-yl)]-N'-(3-fluorobenzyl)urea;
N-[3-(tert-butyl)-1H-pyrazol-5-yl)]-N'-(3,4-dimethoxybenzyl)urea;
N-[3-(tert-butyl)-1H-pyrazol-5-yl)]-N'-(4-chlorobenzyl)urea;
N-[3-(tert-butyl)-1H-pyrazol-5-yl)]-N'-(3,4-dihydroxybenzyl)urea;
N-[3-(tert-butyl)-1H-pyrazol-5-yl)]-N'-(3,4-dimethylbenzyl)urea;
N-[3-(tert-butyl)-1H-pyrazol-5-yl)]-N'-(3-chlorophenethyl)urea; and
pharmaceutically acceptable salts thereof.

28. The pharmaceutical composition of claim 15, which is selected from the group consisting of N-(3-phenethyl-1H-pyrazol-5-yl)-1-pyrrolidinecarboxamide;
4-(1,3-benzodioxol-5-yl-methyl)-N-(3-phenethyl-1H-pyrazol5-yl)-1-piperazinecarboxamide;
N-(3-phenethyl-1H-pyrazol-5-yl)-1-piperazinecarboxamide;
N-(3-phenethyl-1H-pyrazol-5-yl)-4-phenyl-1-piperazinecarboxamide;
N-(3-phenethyl-1H-pyrazol-5-yl)-4-methyl-1-piperazinecarboxamide;
N-(3-phenethyl-1H-pyrazol-5-yl)-4-benzyl-1-piperazinecarboxamide;
N-(3-phenethyl-1H-pyrazol-5-yl)-4-morpholinecarboxamide;
N-(3-phenethyl-1H-pyrazol-5-yl)-1-piperidinecarboxamide;
N-(3-phenethyl-1H-pyrazol-5-yl)-4-(aminomethyl)-1-piperidinecarboxamide;
N-(3-phenethyl-1H-pyrazol-5-yl)-N'-benzylurea;
N-(3-phenethyl-1H-pyrazol-5-yl)-N'-phenethylurea;
N-(3-phenethyl-1H-pyrazol-5-yl)-N'-(3,4-dimethoxyphenethyl)urea;
N-(3-phenethyl-1H-pyrazol-5-yl)-N'-(4-hydroxyphenethyl)urea;
N-(3-phenethyl-1H-pyrazol-5-yl)-N'-propylurea;
N-(3-phenethyl-1H-pyrazol-5-yl)-N'-(4-hydroxybutylurea;
N-(3-phenethyl-1H-pyrazol-5-yl)-4-[2-nitro-4-(trifluoromethyl)phenyl]-1-piperazinecarboxamide; and pharmaceutically acceptable salts thereof.

\* \* \* \* \*

UNITED STATES PATENT AND TRADEMARK OFFICE
CERTIFICATE OF CORRECTION

PATENT NO. : 6,387,900 B1
DATED : May 14, 2002
INVENTOR(S) : Pevarello et al.

It is certified that error appears in the above-identified patent and that said Letters Patent is hereby corrected as shown below:

<u>Title page,</u>
Item [45] and Item [*] Notice should read as follows:
-- [45] **Date of Patent: *May 14, 2002**

[*] Notice: This patent issued on a continued prosecution application filed under 37 CFR 1.53(d), and is subject to the twenty year patent term provisions of 35 U.S.C 154 (a)(2).

Subject to any disclaimer, the term of this patent is extended or adjusted under 35 U.S.C. 154(b) by 0 days. --

Signed and Sealed this

Twenty-second Day of October, 2002

*Attest:*

*Attesting Officer*

JAMES E. ROGAN
*Director of the United States Patent and Trademark Office*